United States Patent
Kaneko et al.

(10) Patent No.: US 11,231,413 B2
(45) Date of Patent: *Jan. 25, 2022

(54) SURROGATE BIOMARKER FOR EVALUATING INTRACEREBRAL AMYLOID β PEPTIDE ACCUMULATION AND METHOD FOR ANALYSIS THEREOF

(71) Applicants: Shimadzu Corporation, Kyoto (JP); National Center for Geriatrics and Gerontology, Obu (JP)

(72) Inventors: Naoki Kaneko, Kyoto (JP); Katsuhiko Yanagisawa, Ryugasaki (JP)

(73) Assignees: Shimadzu Corporation, Kyoto (JP); National Center for Geriatrics and Gerontology, Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/313,376

(22) PCT Filed: May 19, 2015

(86) PCT No.: PCT/JP2015/064386
§ 371 (c)(1),
(2) Date: Nov. 22, 2016

(87) PCT Pub. No.: WO2015/178398
PCT Pub. Date: Nov. 26, 2015

(65) Prior Publication Data
US 2017/0184573 A1    Jun. 29, 2017

(30) Foreign Application Priority Data
May 22, 2014   (JP) .............................. JP2014-106560

(51) Int. Cl.
*G01N 33/53*    (2006.01)
*G01N 33/68*    (2006.01)

(52) U.S. Cl.
CPC ......... *G01N 33/5308* (2013.01); *G01N 33/53* (2013.01); *G01N 33/6896* (2013.01);
(Continued)

(58) Field of Classification Search
CPC ............... G01N 33/5308; G01N 33/53; G01N 2333/4709; G01N 2800/2814; G01N 2800/2821; G01N 2500/00; G01N 2800/52
See application file for complete search history.

(56) References Cited

U.S. PATENT DOCUMENTS

2004/0014142 A1   1/2004   Vanmechelen et al.
2009/0239311 A1*  9/2009   Bibl ................... G01N 33/6896
                                                                436/501

(Continued)

FOREIGN PATENT DOCUMENTS

EP    1865326  A1     12/2007
EP    2088426  B1 *   5/2013   ......... G01N 33/6848
(Continued)

OTHER PUBLICATIONS

Roher AE et al. Amyloid beta peptides in human plasma and tissues and their significance for Alzheimer's disease. Alzheimer's & Dementia, 5:18-29. (Year: 2009).*

(Continued)

*Primary Examiner* — Kimberly Ballard
(74) *Attorney, Agent, or Firm* — Morgan, Lewis & Bockius LLP

(57) ABSTRACT

Provided are a biomarker for evaluating a cerebral Aβ accumulation state using an amyloid precursor protein (APP)-derived peptide in a living body-derived sample as an index, and a method for analysis thereof. A living body-derived sample derived from a test subject is measured, and at least one ratio selected from the group consisting of (Continued)

APP669-711/APP672-713 (Aβ1-42); APP672-709 (Aβ1-38)/APP672-713 (Aβ1-42); APP674-711 (Aβ3-40)/APP672-713 (Aβ1-42); APP672-710 (Aβ1-39)/APP672-713 (Aβ1-42); APP672-711 (Aβ1-40)/APP672-713 (Aβ1-42); and APP672-711 (OxAβ1-40)/APP672-713 (Aβ1-42) is calculated, and when each of the ratios of the test subject is higher than each of standard levels which are ratios of a person having normal cognitive function NC− who is negative for cerebral Aβ accumulation, an accumulation amount of cerebral Aβ of the test subject is determined as larger than an accumulation amount of cerebral Aβ of the person having normal cognitive function NC−.

10 Claims, 23 Drawing Sheets

Specification includes a Sequence Listing.

(52) U.S. Cl.
CPC . *G01N 2333/4709* (2013.01); *G01N 2800/52* (2013.01); *G01N 2800/56* (2013.01)

(56) References Cited

U.S. PATENT DOCUMENTS

| | | | |
|---|---|---|---|
| 2011/0097319 A1 | 4/2011 | Matsubara et al. | |
| 2012/0264642 A1* | 10/2012 | Sarasa Barrio | G01N 33/6896 506/9 |
| 2014/0370619 A1* | 12/2014 | Holtzman | G01N 33/6893 436/501 |
| 2016/0334420 A1 | 11/2016 | Kaneko | |
| 2017/0016910 A1 | 1/2017 | Kaneko | |

FOREIGN PATENT DOCUMENTS

| | | |
|---|---|---|
| JP | 2010-19864 A | 1/2010 |
| JP | 2013-63976 A | 4/2013 |
| WO | 2006/118959 A2 | 11/2006 |
| WO | 2006/118959 A3 | 11/2006 |
| WO | WO-2006/118959 A2 | 11/2006 |
| WO | 2013/096451 A2 | 6/2013 |

OTHER PUBLICATIONS

Kaneko et al. Anal. Chem. 2013, 85:3152-3159. (Year: 2013).*
Lame et al. Anal. Biochem. 2011, 419:133-139. (Year: 2011).*
Lewczuk et al. Biol. Psychiatry, 2004, 55:524-530. (Year: 2004).*
Oe et al. Rapid Commun. Mass Spectrom. 2006, 20:3723-3435. (Year: 2006).*
Smith Clin. Chem. 2012, 58(3):528-530. (Year: 2012).*
Grasso G. Mass Spectrom. Rev. 2011, 30:347-365. (Year: 2011).*
Clarke NJ et al. Detection and quantification of cellularly derived amyloid beta peptides by immunoprecipitation-HPLC-MS. FEBS Lett. 430, 419-423. (Year: 1998).*
Busciglio J et al. Generation of beta-amyloid in the secretory pathway in neuronal and nonneuronal cells. Proc Natl Acad Sci USA, 90, 2092-2096. (Year: 1993).*
Schieb H et al. beta-Amyloid peptide variants in brains and cerebrospinal fluid from amyloid precursor protein (APP) transgenic mice. J. Biol. Chem. 286(39):33747-58. (Year: 2011).*
Bibl M et al. CSF amyloid-beta-peptides in Alzheimer's disease, dementia with Lewy bodies and Parkinson's disease dementia. Brain, 2006, 129, 1177-1187. (Year: 2006).*
Wiltfang J et al. Highly conserved and disease-specific patterns of carboxy-terminally truncated Abeta peptides 1-37/38/39 in addition to 1-40/42 in Alzheimer's disease and in patients with chronic neuroinflammation. J. Neurochem. 2002, 81, 481-496. (Year: 2002).*
Di Domenico F et al. Circulating biomarkers of protein oxidation for Alzheimer disease: Expectations within limits. Biochimica et Biophysics Acta, 2011, 1814, 1785-1795. (Year: 2011).*
Portelius E et al. Characterization of amyloid beta peptides in cerebrospinal fluid by an automated immunoprecipitation procedure followed by mass spectrometry. J. Proteome Res. 2007, 6(11), 4433-4439. (Year: 2007).*
Blennow, et al.; "Alzheimer's disease"; Lancet, 368(9533): 387-403 (Jul. 2006).
Portelius, et al."Determination of beta-amyloid peptide signatures in cerebrospinal fluid using immunoprecipitation-mass spectrometry"; J Proteome Res., 5(4): 1010-1016 (Apr. 2006).
Hampel, et al.; "Biological markers of amyloid beta-related mechanisms in Alzheimer's disease"; Exp Neurol., 223(2): 334-346 (Jun. 2010).
Kaneko, et al.; "Identification and quantification of amyloid beta-related peptides in human plasma using matrix-assisted laser desorption/ionization time-of-flight mass spectrometry"; Proc Jpn Acad Ser B Phys Biol Sci., 90(3):104-117 (2014).
Shimada, et al., "Research on the development of an optical method for preventing the advancement of dementia in MCI and Alzheimer-type dementia patients on the basis of PIB-PET, the relationship between spinal fluid and plasma biomarkers, and inferred background pathology of mild cognitive impairment," FY2007, Report on Comprehensive and Shared Research, 2008, pp. 40-42.
Devanand et al.; "Plasma Aβ and PET PiB binding are inversely related in mild cognitive impairment"; Neurology, 77(2):125-131 (Jun. 2011).
Kaneko, et al.; "Novel plasma biomarker surrogating cerebral amyloid deposition"; Proceedings of the Japan Academy, Series B, 90(9):353-364 (Nov. 2014).
International Preliminary Report on Patentability issued in Application No. PCT/JP2015/064386 dated Dec. 1, 2016.
Graff-Radford et al., "Association of Low Plasma AB42/AB40 Ratios With Increased Imminent Risk for Mild Cognitive Impairment and Alzheimer Disease," Arch Neurol, vol. 64, Mar. 2007, pp. 354-362.
Van Oijen, M., Plasma AB1-40 and AB1-42 and the risk of dementia: a prospective case-cohort study, Lacet Neurology, vol. 8, No. 8, 2006, pp. 655-660.
Bibl et al., "Cerebrospinal Fluid Tau, p-Tau 181 and Amyloid-B38/40/42 in Frontotemporal Dementias and Primary Progressive Aphasias," Dementia and Geriatric Cognitive Disorders, vol. 31, 2011, pp. 37-44.
Bibl et al., "CSF Diagnosis of Alzheimer's disease and dementia with Lewy bodies," Journal of Neural Transmission, vol. 113, 2006, pp. 1771-1778.
Bibl et al., "Stability of amyloid-B peptides in plasma and serum," Electrophoreses, vol. 33, 2012, pp. 445-450.
Partial Supplementary European Search Report issued in corresponding application No. 15 79 6166 dated Dec. 15, 2017.
Extended European Search Report issued in corresponding application No. 15 796 166.5 dated Mar. 19, 2018.
Fukumori et al., "Inhibition of endocytosis activates alternative degradation pathway of betaAPP in cultured cells," Psychogeriatrics, 6: 107-113 (2006).
Kaneko et al., "Novel plasma biomarker surrogating cerebral amyloid deposition," Proceedings of the Japan Academy, Series B, 90 (9): 353-364 (2014).
Keneko et al., "Identification and quantification of amyloid beta-related peptides in human plasma using matrix-assisted laser desorption/ionization time-of-flight mass spectrometry," Proceedings of the Japan Academy, Series B, 90 (3): 104-117(2014).
Liu et al., "Plasma Amyloid-beta as a Biomarker in Alzheimer's Disease: The AIBL Study of Agining," Journal of Alzheimer's Disease, 20: 1233-1242 (2010).
Jack Jr., et al., "An Operational Approach to NIA-AA Criteria for Preclinical Alzheimer's Disease," Annals of Neurology, 71 (6): 765-775 (2012).
Shimohama, "New Diagnostic criteria for Alzheimer's Disease," The Journal of Gerontology, 50:1-8 (2013).
Extended European Search Report issued in related European Patent Application No. 19166974.6 dated May 29, 2019.

(56) References Cited

OTHER PUBLICATIONS

Bibl et al., "Cerebrospinal fluid amyloid-beta 2-42 is decreased in Alzheimer's, but not in frontotemporal dementia," Journal of Neural Transmission, 119: 805-813 (2012).
Bibl et al., "Cerebrospinal Fluid Neurochemical Phenotypes in Vascular Dementias: Original Data and Mini-Review," Dementia and Geriatric Cognitive Disorders, 25:256-265 (2008).
Bibl et al., "Validation of amyloid-beta peptides in CSF diagnosis of neurodegenerative dementias," Molecular Psychiatry, 12: 671-680 (2007).
Partial European Search Report issued in related European Patent Application No. 20199160.1 dated Jan. 20, 2021.
Shimada et al., "Research on the development of an optical method for preventing the advancement of dementia in MCI and Alzheimer-type dementia patients on the basis of PIB-PET, the relationship between spinal fluid and plasma biomarkers, and inferred background pathology of mild cognitive impairment," FY2007, Report on comprehensive and Shared Research, 40-42 (2008) (see English translation of previously submitted document).

\* cited by examiner

(A) APP672-713 (Aβ1-42) / SIL-Aβ1-38

NC- vs NC+, AUC=0.789

(B) APP672-713 (Aβ1-42) / SIL-Aβ1-38

NC- vs MCI, AUC=0.746

(C) APP672-713 (Aβ1-42) / SIL-Aβ1-38

NC- vs AD, AUC=0.864

(D) APP672-713 (Aβ1-42) / SIL-Aβ1-38

NC- vs PIB+, AUC=0.808

(A) APP672-709 (Aβ1-38) / APP672-713 (Aβ1-42)

NC- vs NC+, AUC=0.876

(B) APP672-709 (Aβ1-38) / APP672-713 (Aβ1-42)

NC- vs MCI, AUC=0.777

(C) APP672-709 (Aβ1-38) / APP672-713 (Aβ1-42)

NC- vs AD, AUC=0.757

(D) APP672-709 (Aβ1-38) / APP672-713 (Aβ1-42)

NC- vs PIB+, AUC=0.795

(A) APP674-711 (Aβ3-40) / APP672-713 (Aβ1-42)

NC- vs NC+, AUC=0.886

(B) APP674-711 (Aβ3-40) / APP672-713 (Aβ1-42)

NC- vs MCI, AUC=0.826

(C) APP674-711 (Aβ3-40) / APP672-713 (Aβ1-42)

NC- vs AD, AUC=0.973

(D) APP674-711 (Aβ3-40) / APP672-713 (Aβ1-42)

NC- vs PIB+, AUC=0.906

(A) APP672-710 (Aβ1-39) / APP672-713 (Aβ1-42)

NC- vs NC+, AUC=0.955

(B) APP672-710 (Aβ1-39) / APP672-713 (Aβ1-42)

NC- vs MCI, AUC=0.909

(C) APP672-710 (Aβ1-39) / APP672-713 (Aβ1-42)

NC- vs AD, AUC=0.914

(D) APP672-710 (Aβ1-39) / APP672-713 (Aβ1-42)

NC- vs PIB+, AUC=0.924

(A) APP672-711 (Aβ1-40) / APP672-713 (Aβ1-42)

NC- vs NC+, AUC=0.876

(B) APP672-711 (Aβ1-40) / APP672-713 (Aβ1-42)

NC- vs MCI, AUC=0.803

(C) APP672-711 (Aβ1-40) / APP672-713 (Aβ1-42)

NC- vs AD, AUC=0.743

(D) APP672-711 (Aβ1-40) / APP672-713 (Aβ1-42)

NC- vs PIB+, AUC=0.798

(A) OxAPP672-711 (OxAβ1-40) / APP672-713 (Aβ1-42)

NC- vs NC+, AUC=0.897

(B) OxAPP672-711 (OxAβ1-40) / APP672-713 (Aβ1-42)

NC- vs MCI, AUC=0.843

(C) OxAPP672-711 (OxAβ1-40) / APP672-713 (Aβ1-42)

NC- vs AD, AUC=0.885

(D) OxAPP672-711 (OxAβ1-40) / APP672-713 (Aβ1-42)

NC- vs PIB+, AUC=0.876

(A) APP669-711 / APP672-713 (Aβ1-42)

NC- vs NC+, AUC=0.930

(B) APP669-711 / APP672-713 (Aβ1-42)

NC- vs MCI, AUC=0.966

(C) APP669-711 / APP672-713 (Aβ1-42)

NC- vs AD, AUC=0.997

(D) APP669-711 / APP672-713 (Aβ1-42)

NC- vs PIB+, AUC=0.969

SURROGATE BIOMARKER FOR EVALUATING INTRACEREBRAL AMYLOID ß PEPTIDE ACCUMULATION AND METHOD FOR ANALYSIS THEREOF

TECHNICAL FIELD

The present invention pertains to the brain neuroscience field and the clinical medicine field, and relates to a surrogate biomarker for evaluating a cerebral amyloid β peptide (Aβ) accumulation state, and a method for analysis thereof. More specifically, the present invention relates to a surrogate biomarker for evaluating a cerebral Aβ accumulation state using, as an index, a level of Aβ and Aβ-like peptide generated by decomposition of amyloid precursor protein (APP) in a living body-derived sample, and a method for analysis thereof. The biomarker of the present invention is a marker to be used for, for example, presymptomatic diagnosis, screening for subjects of developing preventive intervention (pre-emptive therapeutic drug administration etc.) and evaluation of drug efficacy of therapeutic drugs and prophylactic drugs regarding Alzheimer's disease.

BACKGROUND ART

Alzheimer's disease (AD) is a principal cause of dementia, and occupies 50 to 60% of the entire dementia. The number of patients suffering from dementia was more than or equal to 24 million in the world in 2001, and is estimated to reach 81 million in 2040 (Non-Patent Document 1). It is considered that Aβ is deeply involved in development of Alzheimer's disease. Aβ is produced as a result of proteolysis of amyloid precursor protein (APP) which is a single-pass transmembrane protein and is composed of 770 amino acid residues, by β-secretase and γ-secretase (see FIG. 1). Appearance of senile plaques due to aggregation of Aβ accompanying fibrosis triggers aggregation and accumulation of tau protein inside neurocytes to cause nerve malfunction and neuronal cell death. It is considered that this results in extreme deterioration of the cognitive ability. It has long been known that Aβ mainly consists of 40 mer (Aβ1-40) and 42 mer (Aβ1-42) and migrates into cerebrospinal fluid (CSF) and blood. Further, in recent years, existence of Aβ-like peptides having lengths different from those of Aβ1-40 and Aβ1-42 in CSF has been reported (Non-Patent Document 2).

Alzheimer's disease develops latently and advances slowly. Diagnosis of Alzheimer's disease is made by performing ADAS-cog, MMSE, DemTect, SKT, or a test of cognitive function such as a clock drawing test for examining the clinical symptom, and examination of image findings of magnetic resonance imaging diagnosis (MRI), positron emission tomography (PET) and the like in combination. While MRI is an image diagnostic method capable of detecting cerebral degenerative atrophy, cerebral atrophy is not specific for Alzheimer's disease. Meanwhile, as an image diagnostic method that visualizes retention of a ligand molecule that specifically detects Aβ deposits (PiB: Pittsburgh compound-B), PiB-PET has been known. It has been found that thioflavin T-analogue (11C) PiB is retained in reflection of Aβ that gradually accumulates in a specific region of the brain of a patient suffering from mild cognitive impairment (MCI) or mild Alzheimer's disease, and hence PiB-PET is an optimum tool for detecting Aβ deposits. From the pathological findings of necropsy of Alzheimer's disease, it is found that a large quantity of senile plaques has already accumulated even in the case of mild cognitive function decline. This leads the inference that aggregation and deposition of Aβ start quite long before exteriorization of dementia, and the result supporting this inference has been reported also in the findings of PiB-PET. However, PET examination requires massive equipment, and requires an expensive examination fee to perform one examination, and thus is not suited as a method that allows the citizen to widely have the examination.

A biomarker in blood or cerebrospinal fluid (CSF) is a useful index capable of detecting the development and progression of a disease on the molecular level. In Alzheimer's disease, a decrease in concentration of Aβ1-42 in CSF or concentration ratio of Aβ1-42/Aβ1-40, and an increase in total tau value or phosphorylation tau value are reported to be a useful diagnostic marker (Patent Document 1: JP-A-2010-19864, Non-Patent Document 3). However, collection of CSF is highly invasive, and is not suited as a method that allows the citizen to widely have the examination.

Under these circumstances, the potentiality of Aβ1-42 existing in blood as an Alzheimer's disease diagnostic marker is expected in a blood examination; however, it has been reported that the relationship between blood Aβ1-42 concentration and Alzheimer's disease development is low unlike the behavior of Aβ1-42 in CSF (Non-Patent Document 3). The reason for this has not been elucidated.

Also, Patent Document 2: JP-A-2013-63976 discloses a monoclonal antibody that does not recognize a soluble Aβ monomer, but specifically binds only to a soluble Aβ oligomer, and also discloses a diagnostic method of Alzheimer's disease using the antibody. The paragraph [0104] of the publication discloses a method in which when the ratio of Aβ oligomer to Aβ monomer in a sample of a subject is higher than that of a normal healthy person, the subject is determined as being a candidate for Alzheimer's disease.

Non-Patent Document 4 discloses existence of 22 kinds of APP-derived Aβ and Aβ-like peptides in human plasma by combination of immunoprecipitation and a mass spectrometer, and also discloses a method for quantifying these Aβ and Aβ-like peptides.

PRIOR ART DOCUMENTS

Patent Documents

Patent Document 1: JP-A-2010-19864
Patent Document 2: JP-A-2013-63976

Non-Patent Documents

Non-Patent Document 1: Blennow K, de Leon M J, Zetterberg H. Alzheimer's disease. Lancet. 2006 Jul. 29; 368 (9533): 387-403
Non-Patent Document 2: Portelius E, Westman-Brinkmalm A, Zetterberg H, Blennow K. Determination of beta-amyloid peptide signatures in cerebrospinal fluid using immunoprecipitation-mass spectrometry. J Proteome Res. 2006 Apr. 5(4): 1010-6
Non-Patent Document 3: Hampel H, Shen Y, Walsh D M, Aisen P, Shaw L M, Zetterberg H, Trojanowski J Q, Blennow K. Biological markers of amyloid beta-related mechanisms in Alzheimer's disease. Exp Neurol. 2010 June; 223(2): 334-46
Non-Patent Document 4: Kaneko N, Yamamoto R, Sato T A, Tanaka K. Identification and quantification of amyloid beta-related peptides in human plasma using matrix-assisted laser desorption/ionization time-of-flight mass spectrometry. Proc Jpn Acad Ser B Phys Biol Sci. 2014; 90(3):104-17

SUMMARY OF THE INVENTION

Problems to be Solved by the Invention

It has been found that a large quantity of Aβ has been deposited before exteriorization of the cognitive function decline in an Alzheimer's disease (AD) patient. Although PiB-PET is effective for detecting Aβ accumulation, it requires high examination cost and long time for executing the examination, and thus is not a diagnostic method that allows for a majority of elderly people to easily undergo the examination. Therefore, a simplified analytical method capable of detecting increase in Aβ accumulation before exteriorization of clinical symptoms has been demanded.

As described above, generally, an examination method using a biomarker existing in blood or cerebrospinal fluid (CSF) as an index is an effective method capable of conveniently detecting the development and progression of a disease on the molecular level. Patent Document 1 and Non-Patent Document 3 described above have reported that in Alzheimer's disease, a decrease in concentration of Aβ1-42 in CSF or concentration ratio of Aβ1-42/Aβ1-40, and an increase in total tau value or phosphorylation tau value are useful diagnostic markers. On the other hand, however, Non-Patent Document 3 has also reported that the relationship between blood Aβ1-42 concentration and AD development is low unlike the case of CSF Aβ1-42.

In previous reports regarding Aβ in blood, the correlatively with AD is examined only for concentrations of two kinds of Aβ1-40 and Aβ1-42 in blood. However, existence of shorter Aβ peptides that are cleaved on the N-terminal side or C-terminal side of Aβ1-40 in CSF have been found besides Aβ1-40 and Aβ1-42 by a combinational method of immunoprecipitation and a mass spectrometer. In blood, it had been technically difficult to detect Aβ that is present in a smaller quantity than in CSF by immunoprecipitation and a mass spectrometer; however, as a result of improvement in the immunoprecipitation, existence of 22 kinds of APP-derived Aβ and Aβ-like peptides in human plasma has been elucidated, and a method for quantifying these peptides has been developed (Non-Patent Document 4).

An object of the present invention is to provide a biomarker for evaluating a cerebral Aβ accumulation state using an amyloid precursor protein (APP)-derived peptide in a living body-derived sample as an index, and a method for analysis thereof. In particular, an object of the present invention is to provide a biomarker for evaluating a cerebral Aβ accumulation state using amyloid precursor protein (APP)-derived Aβ and Aβ-like peptide in a blood sample as an index, and a method for analysis thereof. More specifically, an object of the present invention to provide a marker to be used for, for example, presymptomatic diagnosis, screening for subjects of developing preventive intervention (pre-emptive therapeutic drug administration etc.) and evaluation of drug efficacy of therapeutic drugs and prophylactic drugs regarding Alzheimer's disease, and a method for analysis thereof.

Means for Solving the Problems

As a result of diligent efforts, the present inventors have found that specific APP-derived Aβ and Aβ-like peptide achieve the aforementioned object, and accomplished the present invention.

In the present description, "Aβ" is used as an abbreviation of an amyloid β peptide. That is, "Aβ" includes Aβ1-40 and Aβ1-42. A Peptide other than the Aβ generated by cleavage of amyloid precursor protein (APP) may be referred to as an Aβ-like peptide. Aβ and an Aβ-like peptide that are generated by cleavage of amyloid precursor protein (APP) may be referred to as "APP-derived peptide".

The present invention includes the following aspects.
(1) An analytical method for determining a cerebral Aβ accumulation state, the method comprising:
a measurement step of subjecting a living body-derived sample derived from a test subject to detection of a marker containing:
APP672-713 (Aβ1-42) (SEQ ID NO.: 6), and
at least one selected from the group consisting of APP669-711 (SEQ ID NO.: 7), APP672-709 (Aβ1-38) (SEQ ID NO.: 1), APP674-711 (Aβ3-40) (SEQ ID NO.: 2), APP672-710 (Aβ1-39) (SEQ ID NO.: 3), APP672-711 (Aβ1-40) (SEQ ID NO.: 4), and OxAPP672-711 (OxAβ1-40) (SEQ ID NO.: 5),
to obtain measurement levels of:
APP672-713 (Aβ1-42), and
the at least one selected from the group consisting of APP669-711, APP672-709 (Aβ1-38), APP674-711 (Aβ3-40), APP672-710 (Aβ1-39), APP672-711 (Aβ1-40), and OxAPP672-711 (OxAβ1-40) in the living body-derived sample;
a calculation step of calculating at least one ratio selected from the group consisting of:
a ratio of APP669-711 level to APP672-713 (Aβ1-42) level: APP669-711/APP672-713 (Aβ1-42);
a ratio of APP672-709 (Aβ1-38) level to APP672-713 (Aβ1-42) level: APP672-709 (Aβ1-38)/APP672-713 (Aβ1-42);
a ratio of APP674-711 (Aβ1-40) level to APP672-713 (Aβ1-42) level: APP674-711 (Aβ3-40)/APP672-713 (Aβ1-42);
a ratio of APP672-710 (Aβ3-39) level to APP672-713 (Aβ1-42) level: APP672-710 (Aβ1-39)/APP672-713 (Aβ1-42);
a ratio of APP672-711 (Aβ1-40) level to APP672-713 (Aβ1-42) level: APP672-711 (Aβ1-40)/APP672-713 (Aβ1-42); and
a ratio of OxAPP672-711 (OxAβ1-40) level to APP672-713 (Aβ1-42) level: OxAPP672-711 (OxAβ1-40)/APP672-713 (Aβ1-42); and
an evaluation step of determining that an amount of cerebral Aβ accumulation of the test subject is larger than an amount of cerebral Aβ accumulation of a person having normal cognitive function NC- who is negative for cerebral Aβ accumulation, when each of the ratios of the test subject is higher than each of standard levels which are ratios of the person having normal cognitive function NC-.
(2) The analytical method for determining a cerebral Aβ accumulation state according to the above (1), wherein the living body-derived sample is selected from the group consisting of blood, cerebrospinal fluid, urine, body secreting fluid, feces, saliva, and sputum.
(3) A marker for determining a cerebral Aβ accumulation state, the marker being selected from the group consisting of:
a combination of APP669-711 (SEQ ID NO.: 7) and APP672-713 (Aβ1-42) (SEQ ID NO.: 6),
a combination of APP672-709 (Aβ1-38) (SEQ ID NO.: 1) and APP672-713 (Aβ1-42) (SEQ ID NO.: 6),
a combination of APP674-711 (Aβ3-40) (SEQ ID NO.: 2) and APP672-713 (Aβ1-42) (SEQ ID NO.: 6), a combination of APP672-710 (Aβ1-39) (SEQ ID NO.: 3) and APP672-713 (Aβ1-42) (SEQ ID NO.: 6), a combination of APP672-711 (Aβ1-40) (SEQ ID NO.: 4) and APP672-713 (Aβ1-42) (SEQ ID NO.: 6), and a combination of OxAPP672-711 (OxAβ1-40) (SEQ ID NO.: 5) and APP672-713 (Aβ1-42) (SEQ ID NO.: 6), in a living body-derived sample.

(4) An analytical method for determining a cerebral Aβ accumulation state, the method comprising:

a measurement step of subjecting a blood sample derived from a test subject to detection of a marker containing APP672-713 (Aβ1-42) (SEQ ID NO.: 6), to obtain a measurement level of APP672-713 (Aβ1-42) in the blood sample; and an evaluation step of determining that an amount of cerebral Aβ accumulation of the test subject is larger than an amount of cerebral Aβ accumulation of a person having normal cognitive function NC– who is negative for cerebral Aβ accumulation, when the measurement level of APP672-713 (Aβ1-42) of the test subject is lower than a standard level which is a level of APP672-713 (Aβ1-42) of the person having normal cognitive function NC–.

(5) A method for determining efficacy of a medical intervention regarding a cerebral Aβ accumulation state, the method comprising, before and after a medical intervention performed for a test subject:

a measurement step of subjecting a living body-derived sample derived from the test subject to detection of a marker containing:

APP672-713 (Aβ1-42) (SEQ ID NO.: 6), and at least one selected from the group consisting of APP669-711 (SEQ ID NO.: 7), APP672-709 (Aβ1-38) (SEQ ID NO.: 1), APP674-711 (Aβ3-40) (SEQ ID NO.: 2), APP672-710 (Aβ1-39) (SEQ ID NO.: 3), APP672-711 (Aβ1-40) (SEQ ID NO.: 4), and OxAPP672-711 (OxAβ1-40) (SEQ ID NO.: 5), to obtain measurement levels of:

APP672-713 (Aβ1-42), and the at least one selected from the group consisting of APP669-711, APP672-709 (Aβ1-38), APP674-711 (Aβ1-40), APP672-710 (Aβ1-39), APP672-711 (Aβ1-40), and OxAPP672-711 (OxAβ1-40) in the living body-derived sample; and a calculation step of calculating at least one ratio selected from the group consisting of:

a ratio of APP669-711 level to APP672-713 (Aβ1-42) level: APP669-711/APP672-713 (Aβ1-42);

a ratio of APP672-709 (Aβ1-38) level to APP672-713 (Aβ1-42) level: APP672-709 (Aβ1-38)/APP672-713 (Aβ1-42);

a ratio of APP674-711 (Aβ3-40) level to APP672-713 (Aβ1-42) level: APP674-711 (Aβ3-40)/APP672-713 (Aβ1-42);

a ratio of APP672-710 (Aβ1-39) level to APP672-713 (Aβ1-42) level: APP672-710 (Aβ1-39)/APP672-713 (Aβ1-42);

a ratio of APP672-711 (Aβ1-40) level to APP672-713 (Aβ1-42) level: APP672-711 (Aβ1-40)/APP672-713 (Aβ1-42); and a ratio of OxAPP672-711 (OxAβ1-40) level to APP672-713 (Aβ1-42) level: OxAPP672-711 (OxAβ1-40)/APP672-713 (Aβ1-42); and comparing each of the ratios of the test subject before the medical intervention and each of the ratios of the test subject after the medical intervention to determine efficacy of the medical intervention regarding a cerebral Aβ accumulation state.

In the present invention, the term "level of marker" basically means a concentration, but may be other units applied correspondingly to concentration by a person skilled in the art. The term "test subject" includes human, and mammals other than human (rat, dog, cat etc.). In the present invention, the living body-derived sample is disposed of rather than being returned to the test subject (for example, subject) from which the biological sample is derived. The medical intervention includes administration of a therapeutic drug or a prophylactic drug, dietetic therapy, exercise therapy, learning therapy, surgical operation and the like.

Effects of the Invention

The present invention provides a marker for determining a cerebral Aβ accumulation state of a test subject, including a combination of APP672-713 (Aβ1-42) (SEQ ID NO.: 6) and at least one selected from the group consisting of APP669-711 (SEQ ID NO.: 7), APP672-709 (Aβ1-38) (SEQ ID NO.: 1), APP674-711 (Aβ3-40) (SEQ ID NO.: 2), APP672-710 (Aβ1-39) (SEQ ID NO.: 3), APP672-711 (Aβ1-40) (SEQ ID NO.: 4), and OxAPP672-711 (OxAβ1-40) (SEQ ID NO.: 5) in a living body-derived sample. Also, the present invention provides a method for analysis of the marker.

By analyzing the marker in the living body-derived sample of the test subject, it is possible to discriminate whether cerebral Aβ accumulation in the test subject is less than or equal to the standard level or cerebral Aβ is excessively accumulated. The present invention is applicable to detection of not only the advanced stage of Alzheimer's disease in which cerebral Aβ is excessively accumulated and a cognitive functional disorder has appeared, but also the early stage of Alzheimer's disease in which cerebral Aβ is excessively accumulated but a cognitive functional disorder has not been appeared.

According to the present invention, as the living body-derived sample, not only blood, but also cerebrospinal fluid (CSF), urine, body secreting fluid, feces, saliva, and sputum can be used. Therefore, in the stage where the preventive method and the pre-emptive therapeutic method for Alzheimer's disease have established, analysis of a cerebral Aβ accumulation state for a person having normal cognitive function in a general medical examination, a complete physical examination and the like is effective for presymptomatic diagnosis of Alzheimer's disease.

By applying the present invention before and after a medical intervention performed for the test subject, it is possible to evaluate the drug efficacy of a therapeutic drug or a prophylactic drug for Alzheimer's disease, or to evaluate the efficacy of other treatment. Also, the present invention is useful for follow-up of a patient suffering from Alzheimer's disease.

MODES FOR CARRYING OUT THE INVENTION

[1. Test Subject]

Figure 1:
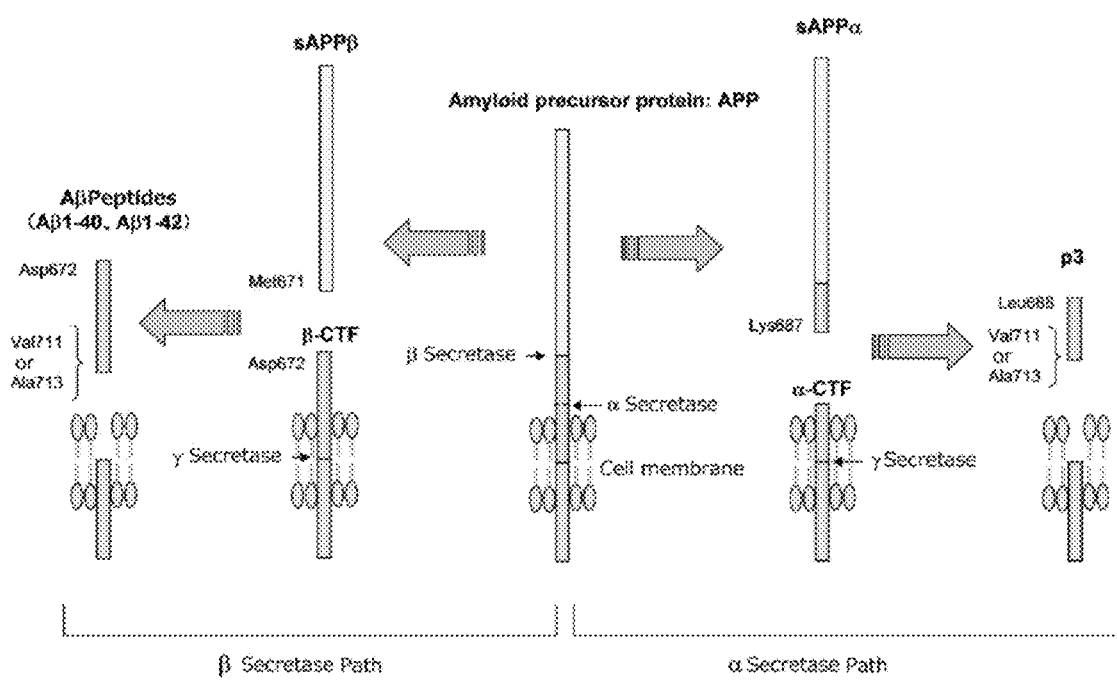
FIG. 1 shows a diagram schematically showing the formation path of Aβ and p3 peptides by cleavages of amyloid precursor protein (APP).

In the present invention, the test subject includes human, and mammals other than human (rat, dog, cat etc.). Hereinafter, the description will be made mainly for the case of human, but the same applies to mammals other than human.

In the method of the present invention, the subject may be any individuals including a person expected to be a normal healthy person regardless of past clinical history. For a person expected to be a normal healthy person, a cerebral Aβ accumulation state can be determined in a general medical examination, or a complete physical examination, preferably by a blood test, and the method is particularly effective for early detection/diagnosis of Alzheimer's disease. For a subject suspected to be a candidate for Alzheimer's disease as a result of ADAS-cog, MMSE, DemTect, SKT, or a test of cognitive function such as a clock drawing test for examining clinical symptom, and confirmation of image findings of magnetic resonance imaging diagnosis (MRI), positron emission tomography (PET) and the like, the method of the present invention can assist the diagnosis of Alzheimer's disease.

[2. Living Body-Derived Sample]

The marker of the present invention can be detected and analyzed in a living body-derived sample of a subject. Therefore, in the method of the present invention, a level of a marker in a living body-derived sample of a subject is analyzed.

The living body-derived sample can be selected from body fluids such as blood, cerebrospinal fluid (CSF), urine, body secreting fluid, saliva, and sputum; and feces. Among these, blood is preferred for diagnosis and presymptomatic diagnosis of Alzheimer's disease in a general medical examination, a complete physical examination or the like.

The blood sample is a sample that is directly subjected to a measurement step of marker level, and includes whole blood, plasma, serum and the like. The blood sample can be prepared by appropriately treating whole blood collected from a test subject. The treatment performed in the case of preparing a blood sample from collected whole blood is not particularly limited, and any treatment that is clinically acceptable may be performed. For example, centrifugal separation or the like may be performed. The blood sample subjected to the measurement step may be appropriately stored at a low temperature such as freezing in the intermediate stage of the preparation step or in the post stage of the preparation step. In the present invention, the living body-derived sample such as a blood sample is disposed of rather than being returned to the subject from which it is derived.

[3. Marker]

The marker of the present invention includes a combination of APP672-713 (Aβ1-42) (SEQ ID NO.: 6) and at least one selected from the group consisting of APP669-711 (SEQ ID NO.: 7), APP672-709 (Aβ1-38) (SEQ ID NO.: 1), APP674-711 (Aβ3-40) (SEQ ID NO.: 2), APP672-710 (Aβ1-39) (SEQ ID NO.: 3), APP672-711 (Aβ1-40) (SEQ ID NO.: 4), and OxAPP672-711 (OxAβ1-40) (SEQ ID NO.: 5) in a living body-derived sample. For these markers, a significant difference has been observed between the level in the plasma sample from a person having normal cognitive function who is negative for cerebral Aβ accumulation and the level in the plasma sample from a subject having excessively accumulated cerebral Aβ.

APP672-713 (Aβ1-42) (SEQ ID NO.: 6):
DAEFRHDSGYEVHHQKLVFFAEDVGSNKGAIIGLMVGGVVIA

APP669-711 (SEQ ID NO.: 7):
VKMDAEFRHDSGYEVHHQKLVFFAEDVGSNKGAIIGLMVGGVV

APP672-709 (Aβ1-38) (SEQ ID NO.: 1):
DAEFRHDSGYEVHHQKLVFFAEDVGSNKGAIIGLMVGG

APP674-711 (Aβ3-40) (SEQ ID NO.: 2):
EFRHDSGYEVHHQKLVFFAEDVGSNKGAIIGLMVGGVV

APP672-710 (Aβ1-39) (SEQ ID NO.: 3):
DAEFRHDSGYEVHHQKLVFFAEDVGSNKGAIIGLMVGGV

APP672-711 (Aβ1-40) (SEQ ID NO.: 4):
DAEFRHDSGYEVHHQKLVFFAEDVGSNKGAIIGLMVGGVV

OxAPP672-711 (OxAβ1-40) (SEQ ID NO.: 5):
DAEERHDSGYEVHHQKLVFFAEDVGSNKGAIIGLMVGGVV
(Met 706 is oxidized)

Amyloid precursor protein (APP) is a single-pass transmembrane protein and is composed of 770 amino acid residues. Amyloid precursor protein (APP) is proteolyzed by β secretase and γ secretase, and an amyloid β peptide (Aβ) is produced by the proteolysis. APP672-713 and Aβ1-42 indicate the same peptide (SEQ ID NO.: 6). APP672-711 and Aβ1-40 indicate the same peptide (SEQ ID NO.: 4).

Table 1 shows amino acid sequences of APP-derived peptides, and Table 2 shows theoretical average masses of the same. For these peptides, analysis of a marker for determining a cerebral Aβ accumulation state was performed.

TABLE 1

| SEQ ID NO. | APP-derived peptides | Sequence VKMDAEFRHDSGYEVHHQKLVFF 669 AEDVGSNKGAIIGLMVGGVVIA 713 |
|---|---|---|
| 1 | APP672-709 (Aβ1-38) | DAEFRHDSGYEVHHQKLVFFAED VGSNKGAIIGLMVGG |
| 2 | APP674-711 (Aβ3-40) | EFRHDSGYEVHHQKLVFFAEDVG SNKGAIIGLMVGGVV |
| 3 | APP672-710 (Aβ1-39) | DAEFRHDSGYEVHHQKLVFFAED VGSNKGAIIGLMVGGV |
| 4 | APP672-711 (Aβ1-40) | DAEFRHDSGYEVHHQKLVFFAED VGSNKGAIIGLMVGGVV |
| 5 | OxAPP672-711 (OxAβ1-40) | DAEERHDSGYEVHHQKLVFFAED VGSNKGAIIGL_MVGGVV |
| 6 | APP672-713 (Aβ1-42) | DAEFRHDSGYEVHHQKLVFFAED VGSNKGAIIGLMVGGVVIA |
| 7 | APP669-711 | VKMDAEFRHDSGYEVHHQKLVFF AEDVGSNKGAIIGLMVGGVV |

TABLE 2

| SEQ ID NO. | Theoretical average mass |
|---|---|
| 1 | 4132.6 |
| 2 | 4144.7 |
| 3 | 4231.8 |
| 4 | 4330.9 |
| 5 | 4346.9 |
| 6 | 4515.1 |
| 7 | 4689.4 |

In Tables 1 to 2, "APP-derived peptides" indicates APP-derived peptides, and "Theoretical average mass" indicates theoretical average mass.

In Tables 1 to 2, OxAPP672-711 (OxAβ1-40) of SEQ ID NO.: 5 indicates a peptide oxidized at Met 706 in APP672-711 (Aβ1-40) of SEQ ID NO.: 4.

In Alzheimer's disease, there is familial Alzheimer's disease. The markers of the present invention may include mutation of familial Alzheimer's disease in the amino acid sequence that is generally known.

For familial Alzheimer's disease, for example, the following mutation sequences are known.

Swedish mutation: Amino acids KM in APP670-671 are mutated into NL.

Italian mutation: Amino acid A at APP673 is mutated into V.

Leuven mutation: Amino acid E at APP682 is mutated into K.

Icelandic mutation: Amino acid A at APP673 is mutated into T.

British mutation: Amino acid H at APP677 is mutated into R.

Tottori mutation: Amino acid D at APP678 is mutated into N.

Arctic mutation: Amino acid E at APP693 is mutated into G.

Iowa mutation: Amino acid D at APP694 is mutated into N.

Dutch mutation: Amino acid E at APP693 is mutated into Q.

[4. Analysis of Marker]

In the present description, the following classification is made from the view point of the degree of advance of Alzheimer's disease.

NC−: a person who is negative for cerebral Aβ accumulation, and does not have a cognitive impairment NC+: a person who is positive for cerebral Aβ accumulation, but does not have a cognitive impairment MCI: a person who is positive for cerebral Aβ accumulation, and has a mild cognitive impairment AD: a person who is positive for cerebral Aβ accumulation, and has a cognitive impairment PiB+: combined group of the group NC+, the group MCI and the group AD; that is, a person determined as positive for cerebral Aβ accumulation regardless of the presence or absence of a cognitive impairment Normally, a cerebral Aβ accumulation state is determined by comparing PiB accumulation amount between the cerebral cortex and the white matter based on a PiB-PET image.

A method for analyzing the marker of the present invention includes:

a measurement step of subjecting a living body-derived sample derived from a test subject to detection of a marker containing APP672-713 (Aβ1-42) (SEQ ID NO.: 6), and at least one selected from the group consisting of APP669-711 (SEQ ID NO.: 7), APP672-709 (Aβ1-38) (SEQ ID NO.: 1), APP674-711 (Aβ3-40) (SEQ ID NO.: 2), APP672-710 (Aβ1-39) (SEQ ID NO.: 3), APP672-711 (Aβ1-40) (SEQ ID NO.: 4), and OxAPP672-711 (OxAβ1-40) (SEQ ID NO.: 5), to obtain measurement levels of APP672-713 (Aβ3-42), and the at least one selected from the group consisting of APP669-711, APP672-709 (Aβ1-38), APP674-711 (Aβ3-40), APP672-710 (Aβ1-39), APP672-711 (Aβ1-40), and OxAPP672-711 (OxAβ1-40) in the living body-derived sample;

a calculation step of calculating at least one ratio selected from the group consisting of:

a ratio of APP669-711 level to APP672-713 (Aβ1-42) level: APP669-711/APP672-713 (Aβ1-42);

a ratio of APP672-709 (Aβ1-38) level to APP672-713 (Aβ1-42) level: APP672-709 (Aβ1-38)/APP672-713 (Aβ1-42);

a ratio of APP674-711 (Aβ3-40) level to APP672-713 (Aβ1-42) level: APP674-711 (Aβ3-40)/APP672-713 (Aβ1-42);

a ratio of APP672-710 (Aβ1-39) level to APP672-713 (Aβ1-42) level: APP672-710 (Aβ1-39)/APP672-713 (Aβ1-42);

a ratio of APP672-711 (Aβ1-40) level to APP672-713 (Aβ1-42) level: APP672-711 (Aβ1-40)/APP672-713 (Aβ1-42); and a ratio of OxAPP672-711 (OxAβ1-40) level to APP672-713 (Aβ1-42) level: OxAPP672-711 (OxAβ1-40)/APP672-713 (Aβ1-42); and an evaluation step of determining that an amount of cerebral Aβ accumulation of the test subject is larger than an amount of cerebral Aβ accumulation of a person having normal cognitive function NC− who is negative for cerebral Aβ accumulation, when each of the ratios of the test subject is higher than each of standard levels which are ratios of the person having normal cognitive function NC−. This makes it possible to determine a cerebral Aβ accumulation state, or to assist the determination.

A method for analyzing the marker of the present invention includes:

a measurement step of subjecting a blood sample derived from a test subject to detection of a marker containing APP672-713 (Aβ1-42) (SEQ ID NO.: 6) to obtain a measurement level of APP672-713 (Aβ1-42) in the blood sample; and an evaluation step of determining that an amount of cerebral Aβ accumulation of the test subject is larger than an amount of cerebral Aβ accumulation of a person having normal cognitive function NC− who is negative for cerebral Aβ accumulation, when the measurement level of APP672-713 (Aβ1-42) of the test subject is lower than a standard level which is a level of APP672-713 (Aβ1-42) of the person having normal cognitive function NC−. This makes it possible to determine a cerebral Aβ accumulation state, or to assist the determination.

The term "level of marker" basically means a concentration, but may be other units applied correspondingly to concentration by a person skilled in the art, for example, a detected ion intensity in the mass spectrometry. In the present invention, the concentration of the marker in the living body-derived sample is analyzed by comparing a measurement value and a standard value. For more accurate analysis, it is preferred that the measurement value and the standard value to be compared are values based on the living body-derived samples prepared in the same conditions (pre-treatment condition, storage condition and the like). As the standard level of the marker, a measurement value for a person having normal cognitive function who is negative for cerebral Aβ accumulation NC− can be used. Alternatively, a concentration standard value established for a person having normal cognitive function who is negative for intracerebral Aβ accumulation NC− may be used as the standard level of the marker.

A marker is measured, preferably, by test based on biological molecule specific affinity. The test based on biological molecule specific affinity is a method well known to a person skilled in the art and is not particularly limited, but is preferably an immunoassay. Specific examples of the immunoassay include competitive and non-competitive assays such as western blotting, radioimmunoassay, ELISA (Enzyme-Linked ImmunoSorbent Assay) (sandwich immunoassay, competitive assay, and direct binding assay are included), immunoprecipitation, precipitation reaction, immunodiffusion, immunoagglutination measurement, complement-binding reaction analysis, immunoradiometric assay, fluorescence immunoassay, and protein A immunoassay. In the immunoassay, an antibody that binds to the marker in a living body-derived sample is detected.

In the present invention, the measurement of the marker may be performed by using an immunoglobulin having an antigen binding site capable of recognizing an amyloid precursor protein (APP)-derived peptide, or an antibody-immobilizing carrier prepared by using an immunoglobulin fragment having an antigen binding site capable of recognizing an amyloid precursor protein (APP)-derived peptide. By immunoprecipitation using the antibody-immobilizing carrier, a peptide in the sample can be detected by a mass spectrometer (Immunoprecipitation-Mass Spectrometry: IP-MS).

As shown in the section of EXAMPLES, a blood sample derived from a test subject is subjected to detection of a marker containing APP672-713 (Aβ1-42) (SEQ ID NO.: 6) to obtain a measurement level of APP672-713 (Aβ1-42) in the blood sample; and an amount of cerebral Aβ accumulation of the test subject is determined to be larger than an amount of cerebral Aβ accumulation of a person having normal cognitive function NC− who is negative for cerebral Aβ accumulation, when the measurement level of APP672-713 (Aβ1-42) of the test subject is lower than a standard level which is a level of APP672-713 (Aβ1-42) of the person having normal cognitive function NC−.

EXAMPLES

Hereinafter, the present invention will be described specifically with reference to examples, but is not limited to these examples. In the following, the amount of a matter indicated by % is based on weight when the matter is a subject, and based on volume when the matter is liquid unless otherwise indicated.

Experimental Example 1

(1) Evaluation of Performance of Alzheimer's Disease Diagnosis by Marker of Present Invention Using Clinical Sample Plasma samples of cases classified into groups of NC−, NC+, MCI, and AD were prepared at National Center for Geriatrics and Gerontology.

NC−: a person who is negative for cerebral Aβ accumulation, and does not have a cognitive impairment NC+: a person who is positive for cerebral Aβ accumulation, but does not have a cognitive impairment MCI: a person who is positive for cerebral Aβ accumulation, and has a mild cognitive impairment AD: a person who is positive for cerebral Aβ accumulation, and has a cognitive impairment PiB+: combined group of the group NC+, the group MCI, and the group AD; that is, a person determined as positive for cerebral Aβ accumulation regardless of the presence or absence of a cognitive impairment In order to determine the positivity or negativity of cerebral Aβ accumulation, PiB-PET images of the brains of the subjects were acquired. When the PiB accumulation amount of the cerebral cortex is larger than or equivalent to the non-specific PiB accumulation amount of the white matter, the subject was determined as positive. When only non-specific accumulation to the white matter was observed, and little accumulation was observed in the cortex, the subject was determined as negative. The cognitive impairment was determined in conformity with the NIA-AA criteria published in 2011.

Table 3 shows the feature and the number of cases of each group.

TABLE 3

Outline of Clinical Sample

| Group | n | PiB-PET | Dementia |
|---|---|---|---|
| NC− | 22 | − | − |
| NC+ | 11 | + | − |
| MCI | 12 | + | + |
| AD | 17 | + | ++ |

When the application to early diagnosis of Alzheimer's disease is considered, it is supposed that a blood marker showing variation in measurement level in the NC+ group, which is determined as positive for cerebral Aβ accumulation although does not have a cognitive impairment in comparison with the NC− group, is effective for diagnosis. In other words, it is important to find a blood marker having a diagnostic performance capable of discriminating between the positivity and the negativity of cerebral Aβ accumulation. From this viewpoint, criteria for evaluation were made in the marker analysis whether there is a difference in measurement level between each of other groups and the NC− group.

(2) Preparation of Antibody-Immobilizing Beads

250 μg of anti-Aβ antibody (6E10: Covance) recognizing the residues 3-8 of Aβ as an epitope was digested with 1250 μL of Ficin agarose beads (Thermo) (33% slurry), and 100 μg of anti-Aβ antibody (4G8: Covance) recognizing the residues 18-22 of Aβ as an epitope was digested with 500 ng of lysyl endopeptidase (LysC), and respective digests were separated and collected by size exclusion chromatography. The fractionated sample was examined by reducing and non-reducing SDS-PAGE, and a fraction corresponding to F(ab')$_2$ was pooled. These F(ab')$_2$ fractions of 6E10 and 4G8 were respectively reduced by 30 mM cysteamine to obtain F(ab'). Then 5 μL (amount of beads 150 μg) of amino magnetic beads (Dynabeads M-270 Amine: Invitrogen) was prepared, and PEG and the beads were covalently bound by causing NHS groups of SM(PEG)$_{24}$ to react with amino groups bound onto the surface of the beads at room temperature for 30 minutes. To SM(PEG)$_{24}$ bound to magnetic beads, each 0.25 μg of 6E10 F(ab') and 4G8 F(ab') were added at the same time, and they were caused to react at room temperature for 2 hours to covalently bind a maleimide group and a thiol group. Finally, 0.4 mM L-cysteine was caused to react at room temperature for 30 minutes to block maleimide groups. The prepared antibody-immobilizing beads were stored at 4° C. before use.

(3) Preparation of Internal Standard Peptide

As an internal standard peptide, Aβ1-38 (referred to as SIL-Aβ1-38) that is a stable isotope-labeled AnaSpec (San Jose, Calif., USA) was used. In SIL-Aβ1-38, carbon atoms in Phe and Ile are substituted by $^{13}C$. After dissolving a dry product of SIL-Aβ1-38 in 50 mM NaOH, size exclusion chromatography (SEC) was performed by a Prominence HPLC System (Shimadzu Corp, Kyoto, Japan) installed with a COSMOSIL® 5Diol-120-II [7.5 mm I.D.×600 mm] column (Nacalai Tesque, Kyoto). The settings were as follows: mobile phase: 40 mM Tris-HCl, pH 8.0, flow rate: 1 mL/min, column temperature: 25° C., detection wavelength: 214/280 nm. Part of the collected fractions was subjected to 15-20% Tricine-SDS-PAGE in non-reducing condition, and bands were stained with Silver Staining kit (Invitrogen, Carlsbad, Calif., USA). The fraction identified as a monomer was diluted with 40 mM Tris-HCl, 150 mM NaCl, pH 8.0 containing 1 mg/mL bovine serum albumin, and then dispensed and stored at −80° C. Part of this was taken out, and the concentration of SIL-Aβ1-38 was measured by using a Human Amyloid β (1-38) (FL) Assay Kit (Immuno-Biological Laboratories; Gunma, Japan).

(4) Measurement of Plasma Aβ and Aβ-Like Peptides

For a total of 62 cases, IP-MS was performed by using antibody-immobilizing beads with the use of SIL-Aβ1-38 as the internal standard peptide.

Immunoprecipitation was performed in the following manner.

Into 250 μL of human plasma, 250 μL of a binding buffer (0.2% (w/v) n-Dodecyl-β-D-maltoside (DDM), 0.2% (w/v) n-Nonyl-β-D-thiomaltoside (NTM), 800 mM GlcNAc, 100 mM Tris-HCl, 300 mM NaCl, pH 7.4) containing 10 pM SIL-Aβ1-38 was mixed. The precipitate contained in the plasma sample was centrifugally removed by using Ultrafree-MC, DV 0.65 μm, centrifugal filter devices. 500 μL of Protein G Plus Agarose (50% slurry; Pierce, Rockford, Ill.) was washed once with 400 μL of H$_2$O, and then washed three times with 400 μL of a washing buffer (0.1% (w/v) DDM, 0.1% (w/v) NTM, 50 mM Tris-HCl, 150 mM NaCl, pH 7.4). Into the resultant Protein G Plus Agarose, the previously obtained plasma sample was mixed, and incubated at 4° C. for 1 hour. After removing the Protein G Plus Agarose from the plasma sample, the plasma sample was mixed into 150 μg of antibody-immobilizing beads that was washed twice with an OTG-glycine buffer (1% n-Octyl-β-D-thioglucoside (OTG), 50 mM glycine, pH 2.8) and three times with 100 μL of a washing buffer, and the mixture was incubated at 4° C. for 1 hour to capture Aβ and Aβ-like peptides. Thereafter, the beads were washed once with 500 μL of a washing buffer, four times with 100 μL of a washing buffer, and twice with 20 μL of 50 mM ammonium acetate. Further, after washing once with 20 μL it of H$_2$O, Aβ and Aβ-like peptides captured on the antibody-immobilizing beads were eluted with 2.5 μL of 70% acetonitrile containing 5 mM hydrochloric acid. Each 0.5 μL of the eluate was dropped into 4 wells on a μFocus MALDI Plate™ 900 μm. After mixing 0.5 μL of a matrix solution (0.5 mg/mL CHCA, 0.2% (w/v) MDPNA), measurement was performed by Linear TOF MS.

As a measurement value of Aβ and Aβ-like peptides in plasma, an averaged value of peak intensity ratios of each of Aβ and Aβ-like peptides to the internal standard peptide (SIL-Aβ1-38) obtained in 4 wells measured by Linear TOF was used. For correcting a signal variation in MS peak intensity, the following criteria were provided. Four mass spectra are acquired in one time immunoprecipitation, and thus four peak intensity ratios are obtained for one peptide. A peak intensity ratio that is out of 0.7 to 1.3 times the median of the four peak intensity ratios in a certain peptide is regarded as an outlier, and is not used in the data processing for averaging. While the number of data of peak intensity ratio used for averaging of a certain peptide is four at maximum, the number of data decreases when the peak intensity is less than the detection limit (S/N<3), or an outlier arises. When the number of data of peak intensity ratio used in averaging is less than three, the intensity ratio at the peak is defined as not detectable (N/D) in the immunoprecipitation at that time.

Figure 2:
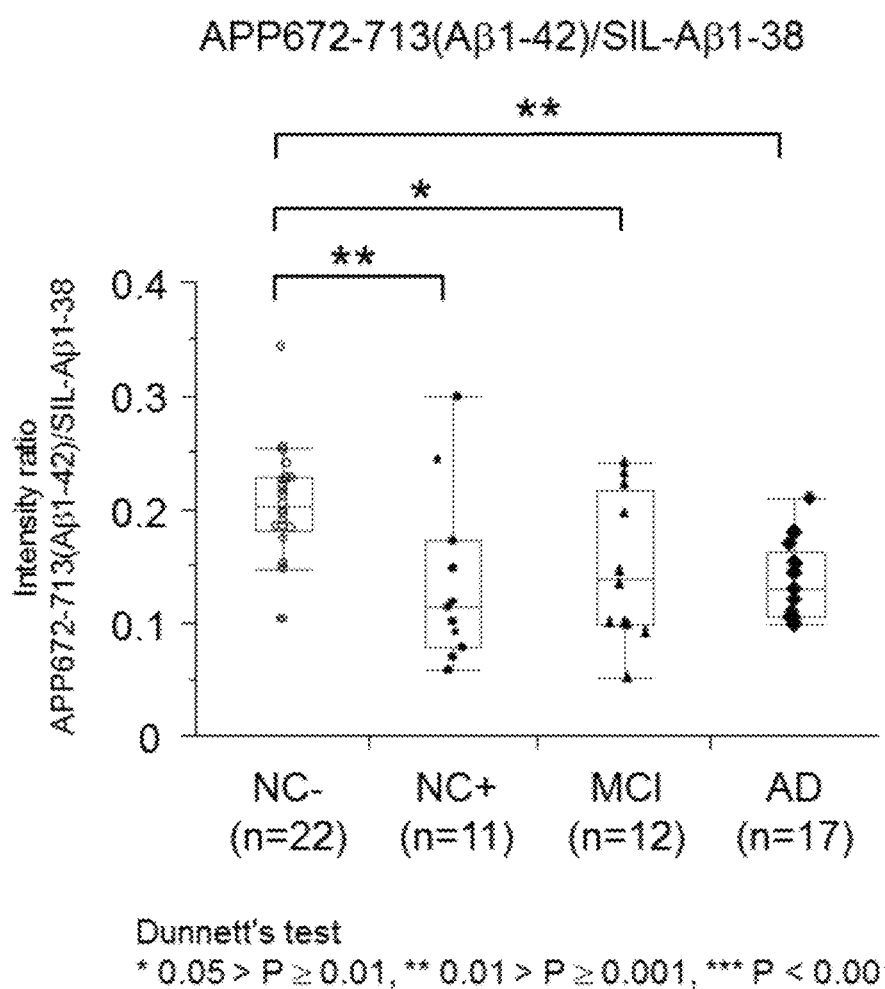
FIG. 2 is a box-and-whisker plot showing the intensity ratio of APP672-713 (Aβ1-42) to the internal standard SIL-Aβ1-38 in each group (NC–, NC+, MCI, AD) for APP672-713 (Aβ1-42) in Example 1.
Figure 3:
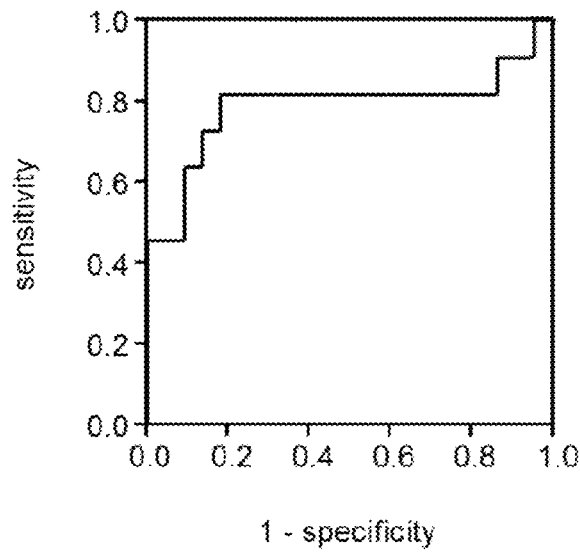
FIG. 3(A) and FIG. 3(B) each show a receiver operatorating characteristic (ROC) curve of each group (NC+, MCI) versus NC– group for APP672-713 (Aβ1-42)/SIL-Aβ1-38.
Figure 3:
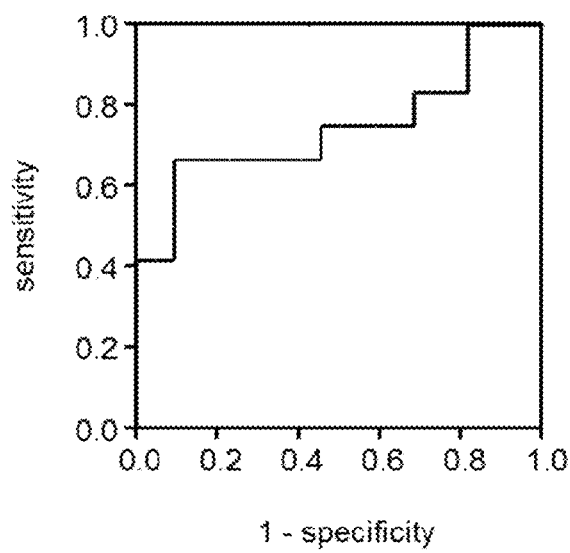
Figure 4:
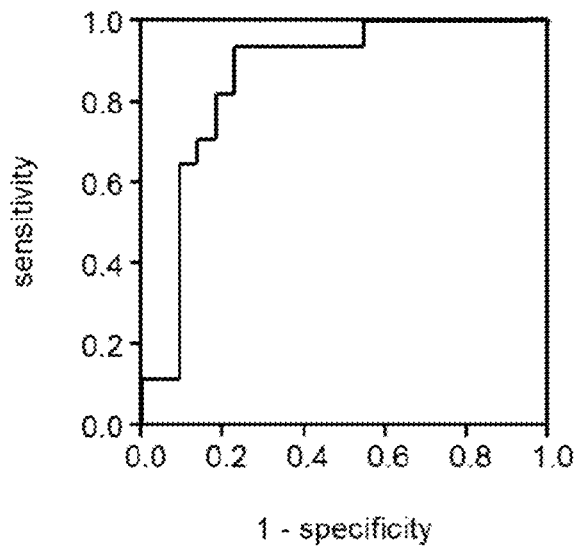
FIG. 4(C) and FIG. 4(D) each show an ROC curve of each group (AD, PiB+) versus NC− group for APP672-713 (Aβ1-42)/SIL-Aβ1-38.
Figure 4:
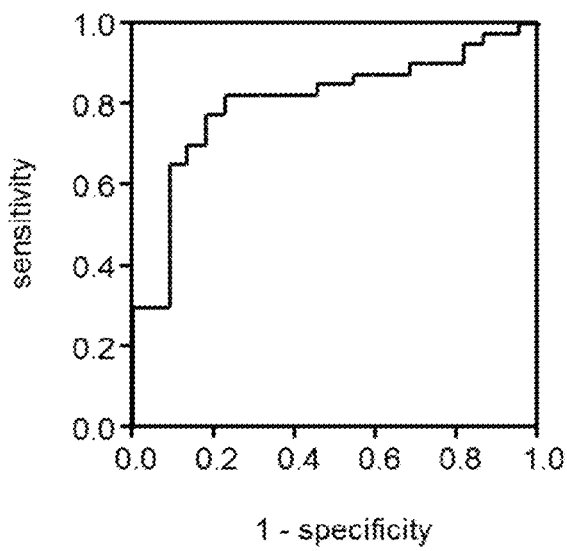

FIG. 2 is a box-and-whisker plot showing the intensity ratio of APP672-713 (Aβ1-42) to the internal standard SIL-Aβ1-38 in each group for APP672-713 (Aβ1-42). FIG. 3(A), FIG. 3(B), FIG. 4(C), and FIG. 4(D) each show an ROC curve of each group (NC+, MCI, AD, PiB+) versus NC− group for APP672-713 (Aβ1-42)/SIL-Aβ1-38.

In each box-and-whisker plot, the range indicated by the box in each group represents the intensity ratio contribution range (quartile range) of the samples whose concentration is rated between 25 to 75% of all specimens, and the horizontal lines shown above and below the box respectively indicate the maximum value and the minimum value of the samples within the range from the upper end and the lower end of the box to 1.5 times the quartile range, and the horizontal bar in the box indicates the median of the intensity ratio.

A statistical significant difference between each of other groups and NC− group was tested by using a Dunnett's test, and it was determined that there is a significant difference when P<0.05. The detection limit or lower was set at 0. As a result, nine kinds of Aβ and Aβ-like peptides were detected in 60% or more cases, and among these, in APP672-713 (Aβ1-42), there was a statistical significant difference in NC+, MCI, and AD in comparison with NC− (FIG. 2). For evaluating the diagnostic performance of APP672-713 (Aβ1-42), ROC curves of NC+, MCI, AD, PiB+ groups versus NC− group were prepared. The areas under ROC curves (AUC) were NC− vs NC+=0.789, NC− vs MCI=0.746, NC− vs AD=0.864, NC− vs PiB+=0.808, and showed relatively high values (FIG. 3(A), FIG. 3(B), FIG. 4(C), and FIG. 4(D)).

As shown in FIG. 2, for APP672-713 (Aβ1-42), the intensity ratio APP672-713 (Aβ1-42)/SIL-Aβ1-38 decreased in NC+, MCI, and AD with a statistical significant difference in comparison with NC−. As shown in FIG. 3(A), FIG. 3(B), FIG. 4(C), and FIG. 4(D), the AUC: NC− vs NC+=0.789, NC− vs MCI=0.746, NC− vs AD=0.864 revealed that APP672-713 (Aβ1-42) had a relatively high ability capable of discrimination between NC− and NC+, NC− and MCI, and NC− and AD. The NC− vs PiB+=0.808 revealed that the performance capable of detecting the subject who is positive for cerebral Aβ accumulation is relatively high. Accordingly, this suggests that APP672-713 (Aβ1-42) is a blood marker capable of estimating a cerebral Aβ accumulation state, and thus it has the possibility capable of being used for assisting diagnosis of Alzheimer's disease.

(5) More Specific Analysis

For observing a clearer difference between each group (NC+, MCI, AD) and NC−, the following investigation was further per formed.

Figure 5:
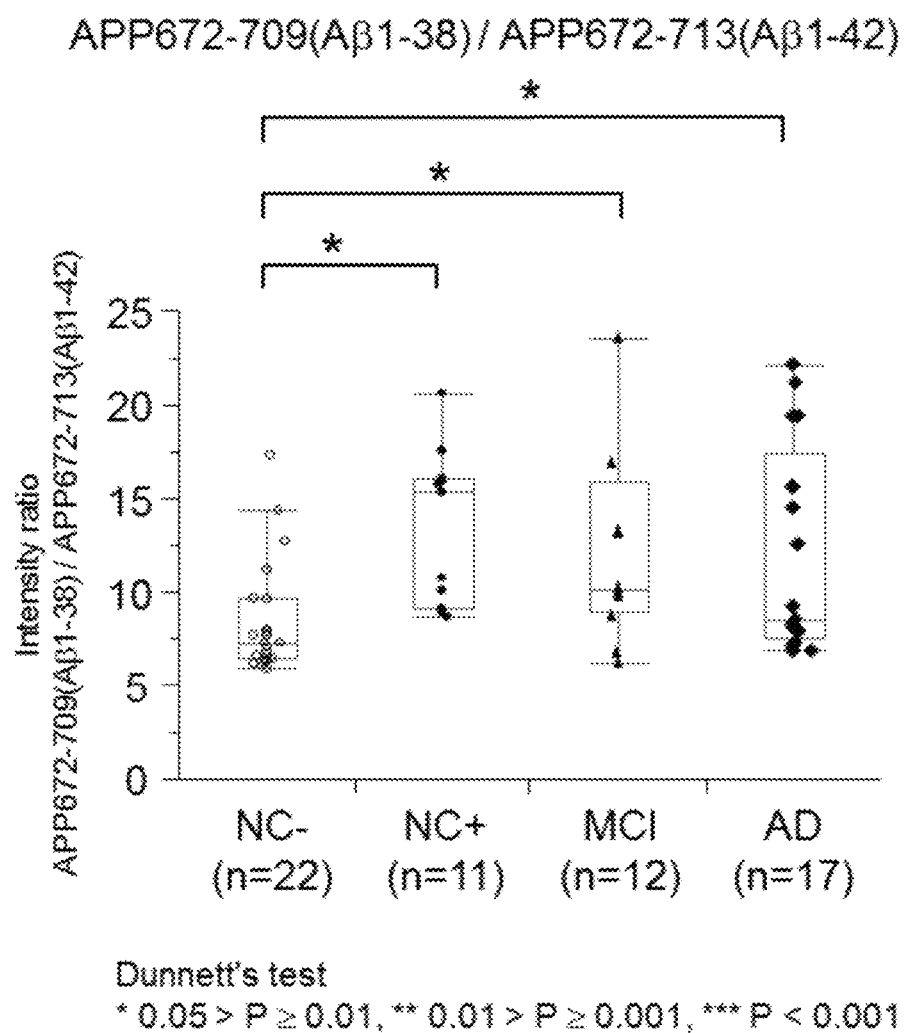
FIG. 5 is a box-and-whisker plot showing the intensity ratio of APP672-709 (Aβ1-38) to APP672-713 (Aβ1-42) in each group (NC−, NC+, MCI, AD) in Example 1.
Figure 6:
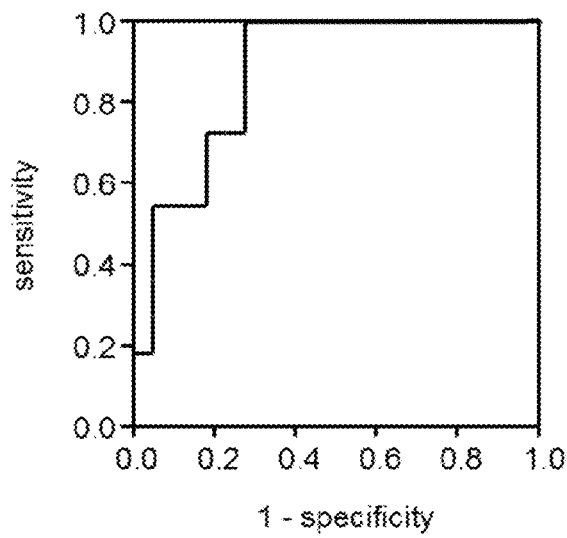
FIG. 6(A) and FIG. 6(B) each show an ROC curve of each group (NC+, MCI) versus NC− group for APP672-709 (Aβ1-38)/APP672-713 (Aβ1-42).
Figure 6:
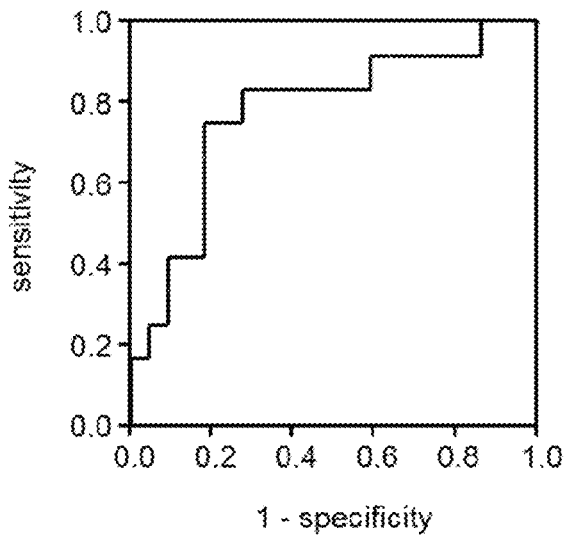
Figure 7:
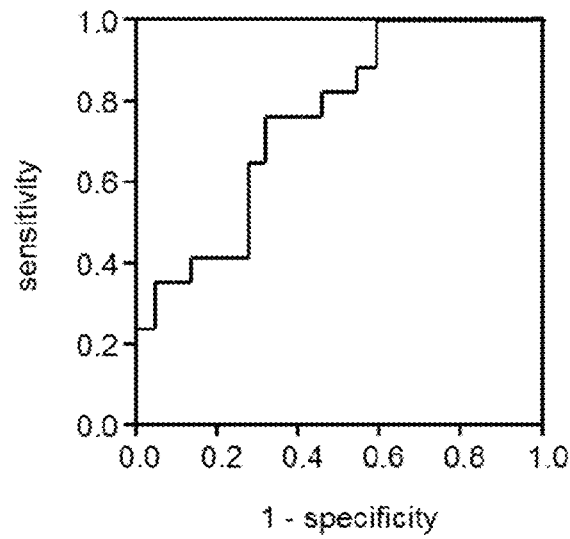
FIG. 7(C) and FIG. 7(D) each show an ROC curve of each group (AD, PiB+) versus NC− group for APP672-709 (Aβ1-38)/APP672-713 (Aβ1-42).
Figure 7:
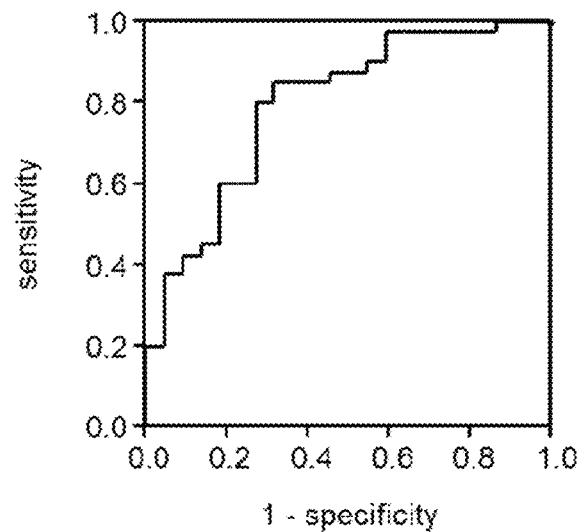

FIG. 5 is a box-and-whisker plot showing the intensity ratio of APP672-709 (Aβ1-38) to APP672-713 (Aβ1-42) in each group. FIG. 6(A), FIG. 6(B), FIG. 7(C), and FIG. 7(D) each show an ROC curve of each group (NC+, MCI, AD, PiB+) versus NC− group for APP672-709 (Aβ1-38)/APP672-713 (Aβ1-42).

Figure 8:
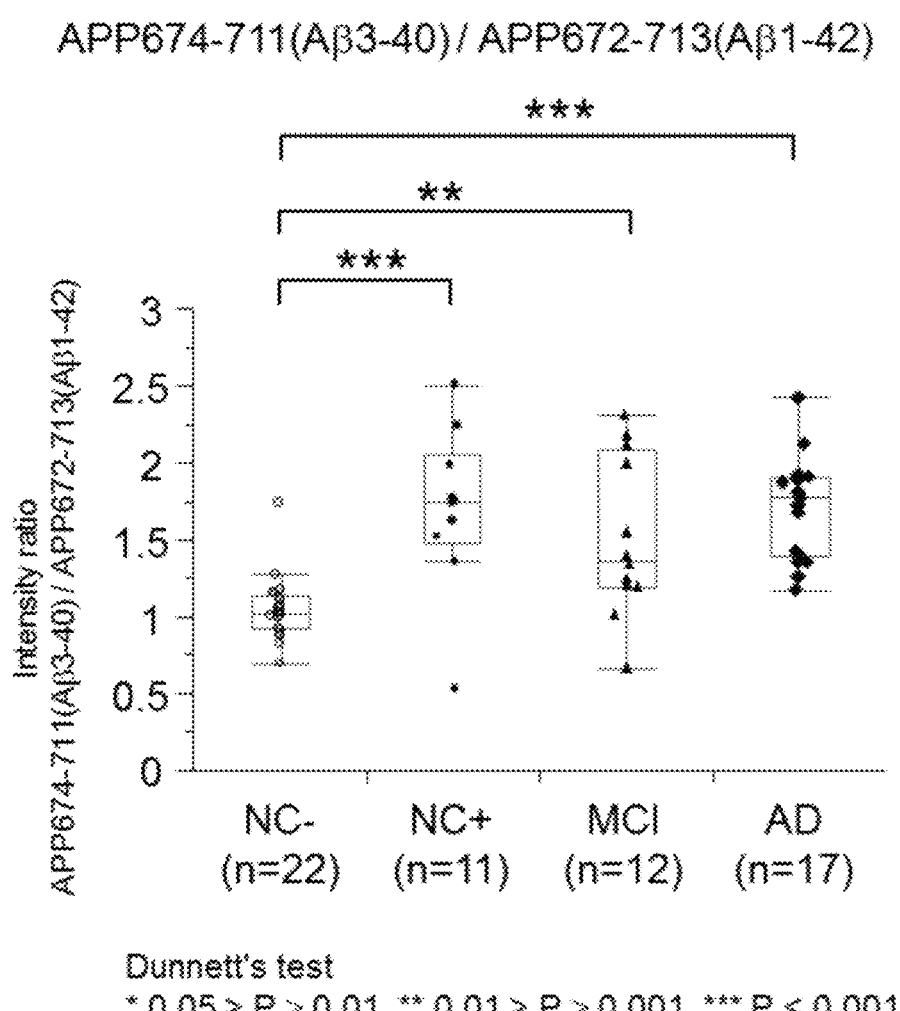
FIG. 8 is a box-and-whisker plot showing the intensity ratio of APP674-711 (Aβ3-40) to APP672-713 (Aβ1-42) in each group (NC−, NC+, MCI, AD) in Example 1.
Figure 9:
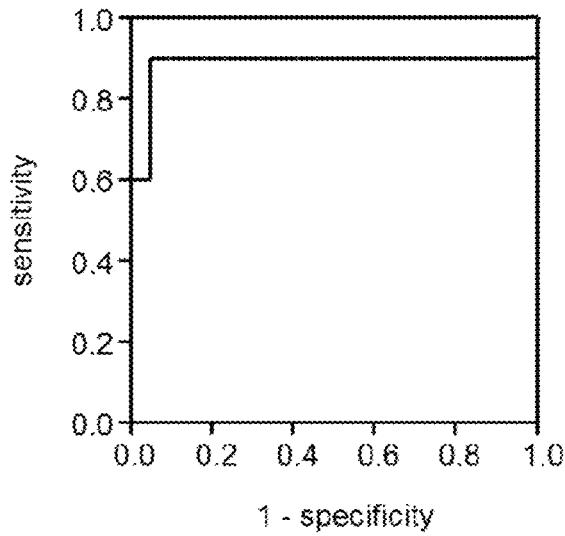
FIG. 9(A) and FIG. 9(B) each show an ROC curve of each group (NC+, MCI) versus NC− group for APP674-711 (Aβ3-40)/APP672-713 (Aβ1-42).
Figure 9:
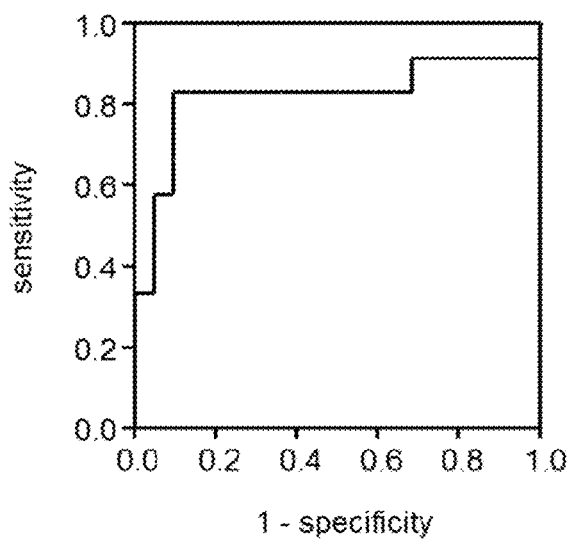
Figure 10:
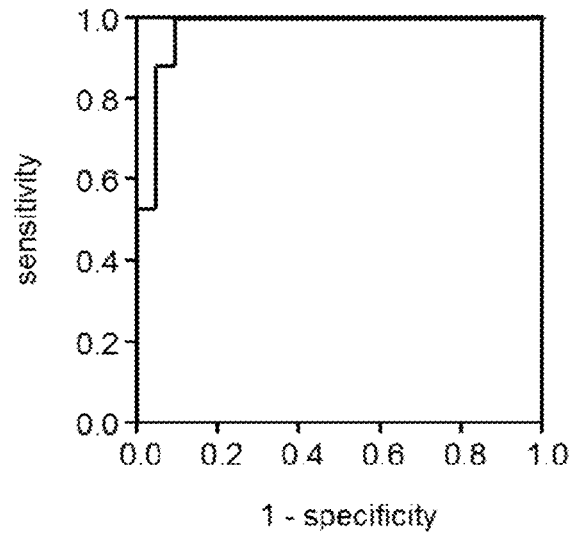
FIG. 10(C) and FIG. 10(D) each show an ROC curve of each group (AD, PiB+) versus NC− group for APP674-711 (Aβ3-40)/APP672-713 (Aβ1-42).
Figure 10:
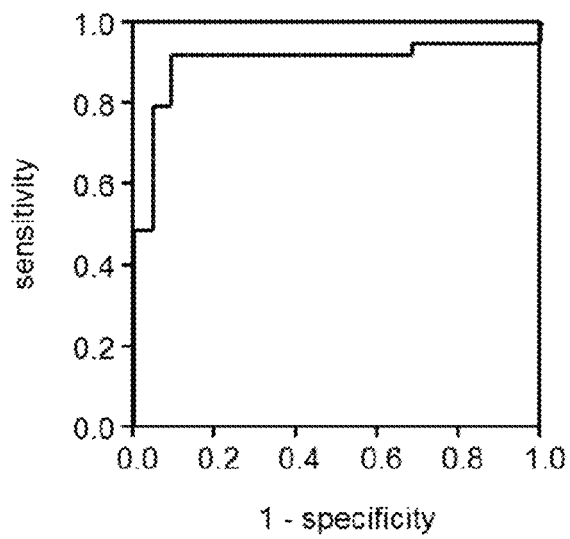

FIG. 8 is a box-and-whisker plot showing the intensity ratio of APP674-711 (Aβ3-40) to APP672-713 (Aβ1-42) in each group. FIG. 9(A), FIG. 9(B), FIG. 10(C), and FIG. 10(D) each show an ROC curve of each group (NC+, MCI, AD, PiB+) versus NC− group for APP674-711 (Aβ3-40)/APP672-713 (Aβ1-42).

Figure 11:
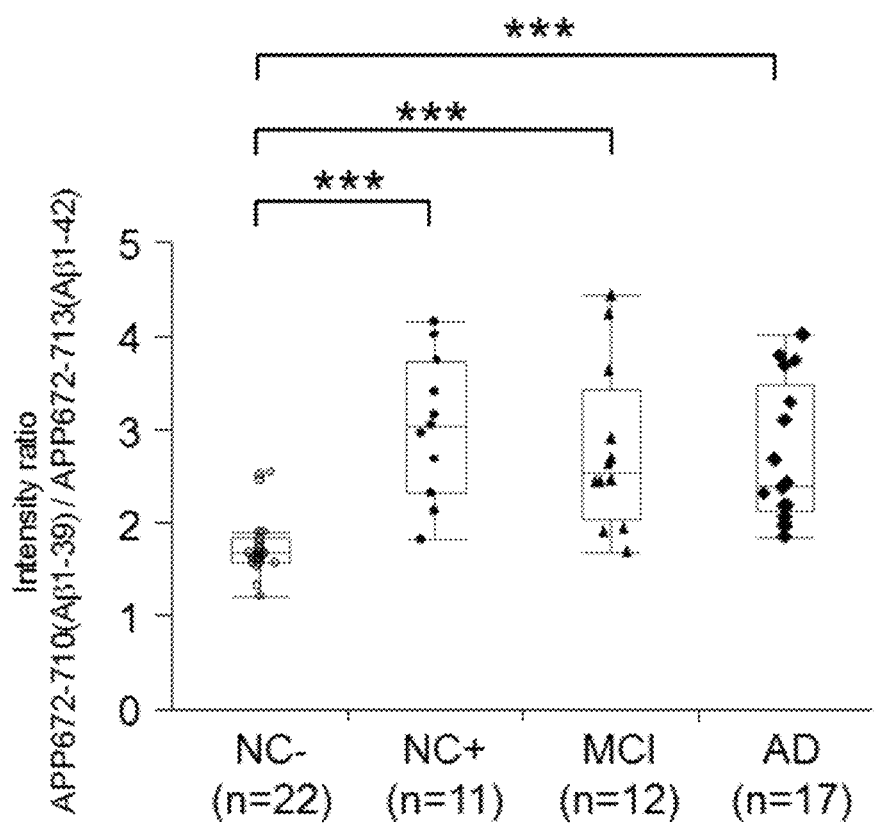
FIG. 11 is a box-and-whisker plot showing the intensity ratio of APP672-710 (Aβ1-39) to APP672-713 (Aβ1-42) in each group (NC−, NC+, MCI, AD) in Example 1.
Figure 12:
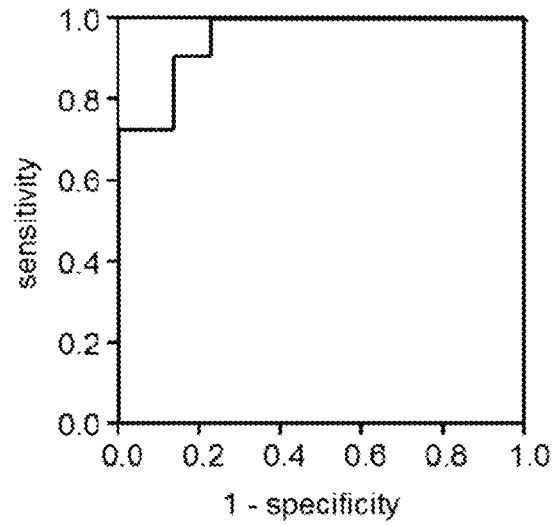
FIG. 12(A) and FIG. 12(B) each show an ROC curve of each group (NC+, MCI) versus NC− group for APP672-710 (Aβ1-39)/APP672-713 (Aβ1-42).
Figure 12:
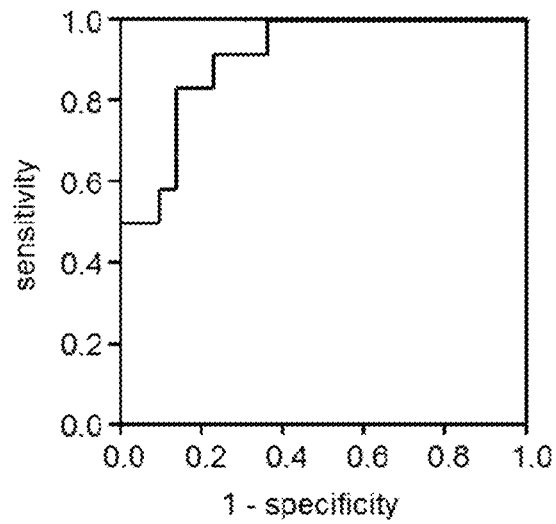
Figure 13:
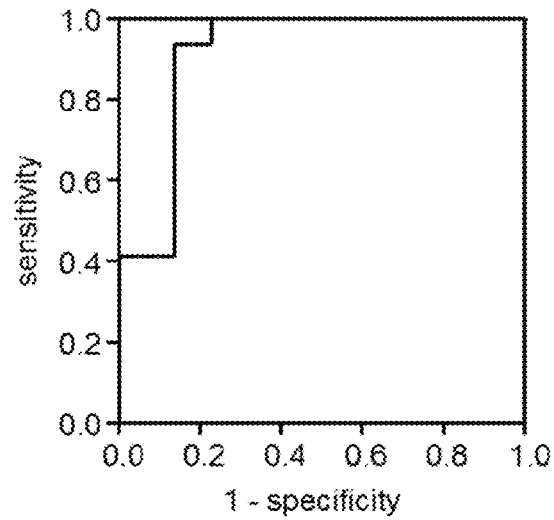
FIG. 13(C) and FIG. 13(D) each show an ROC curve of each group (AD, PiB+) versus NC− group for APP672-710 (Aβ1-39)/APP672-713 (Aβ1-42).
Figure 13:
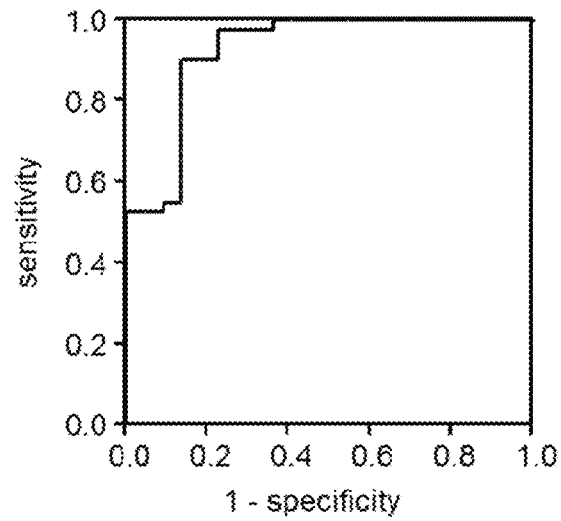

FIG. 11 is a box-and-whisker plot showing the intensity ratio of APP672-710 (Aβ1-39) to APP672-713 (Aβ1-42) in each group. FIG. 12(A), FIG. 12(B), FIG. 13(C), and FIG. 13(D) each show an ROC curve of each group (NC+, MCI, AD, PiB+) versus NC− group for APP672-710 (Aβ1-39)/APP672-713 (Aβ1-42).

Figure 14:
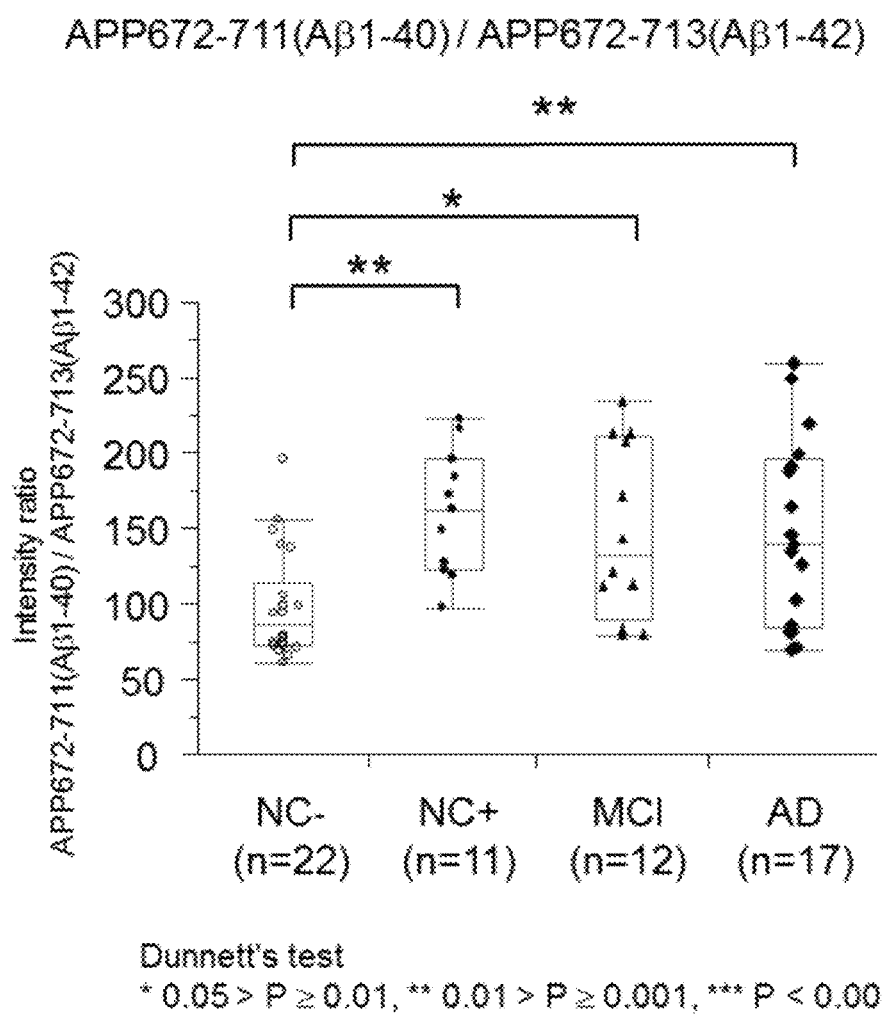
FIG. 14 is a box-and-whisker plot showing the intensity ratio of APP672-711 (Aβ1-40) to APP672-713 (Aβ1-42) in each group (NC−, NC+, MCI, AD) in Example 1.
Figure 15:
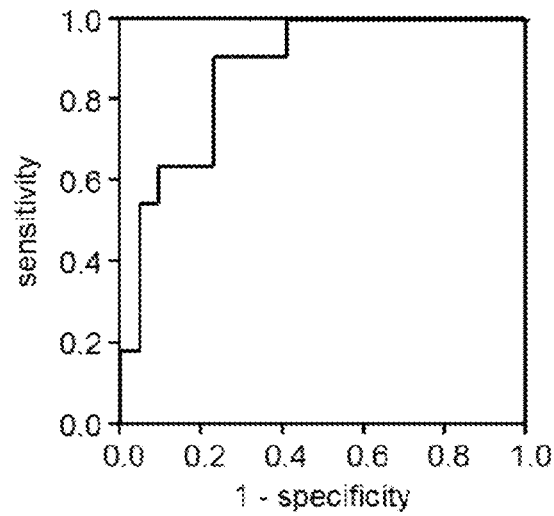
FIG. 15(A) and FIG. 15(B) each show an ROC curve of each group (NC+, MCI) versus NC− group for APP672-711 (Aβ1-40)/APP672-713 (Aβ1-42).
Figure 15:
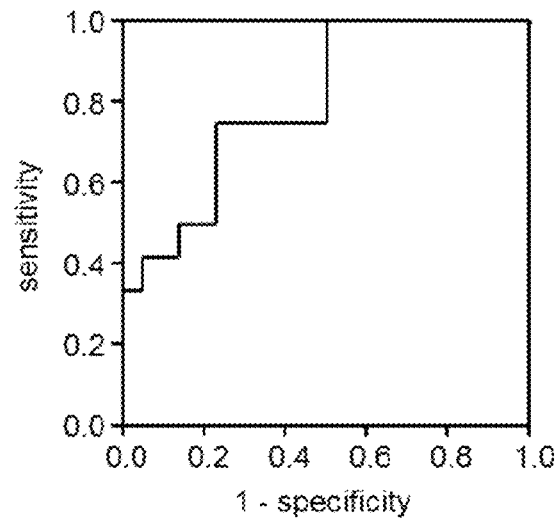
Figure 16:
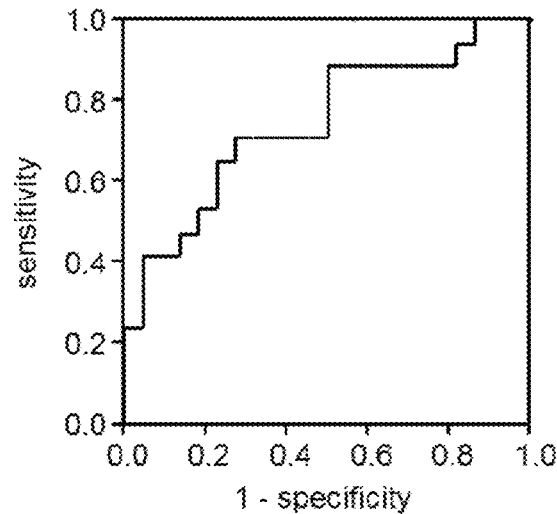
FIG. 16(C) and FIG. 16(D) each show an ROC curve of each group (AD, PiB+) versus NC− group for APP672-711 (Aβ1-40)/APP672-713 (Aβ1-42).
Figure 16:
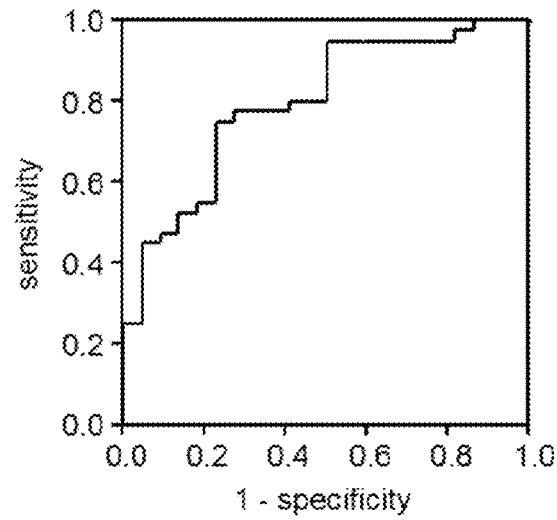

FIG. 14 is a box-and-whisker plot showing the intensity ratio of APP672-711 (Aβ1-40) to APP672-713 (Aβ1-42) in each group. FIG. 15(A), FIG. 15(B), FIG. 16(C), and FIG. 16(D) each show an ROC curve of each group (NC+, MCI, AD, PiB+) versus NC− group for APP672-711 (Aβ1-40)/APP672-713 (Aβ1-42).

Figure 17:
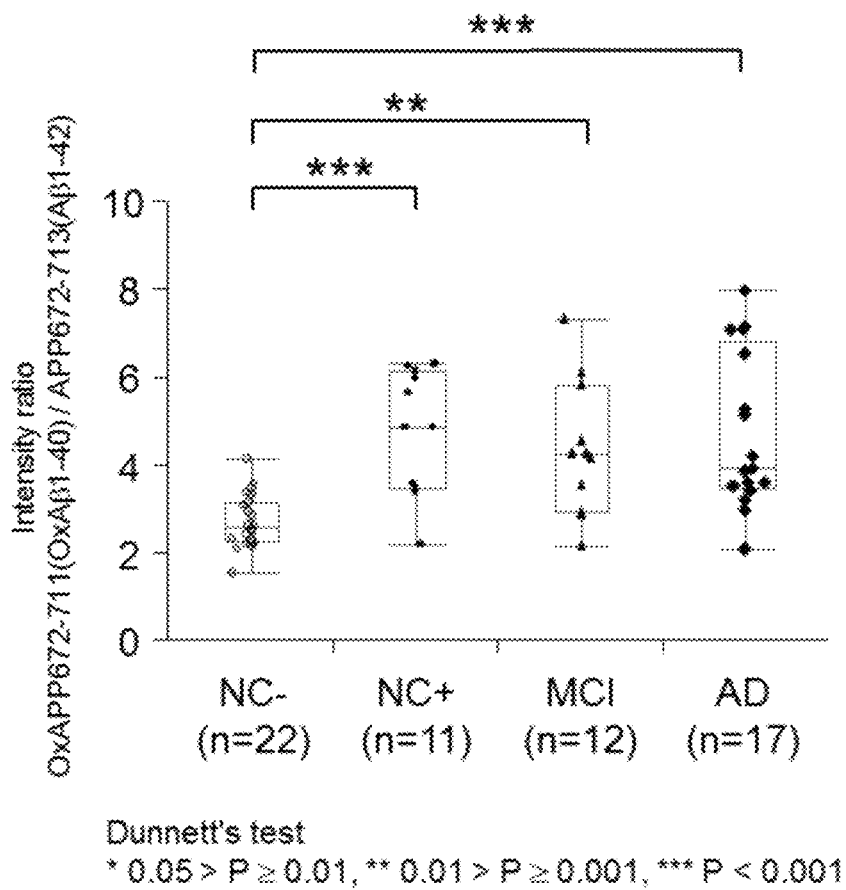
FIG. 17 is a box-and-whisker plot showing the intensity ratio of OxAPP672-711 (OxAβ1-40) to APP672-713 (Aβ1-42) in each group (NC−, NC+, MCI, AD) in Example 1.
Figure 18:
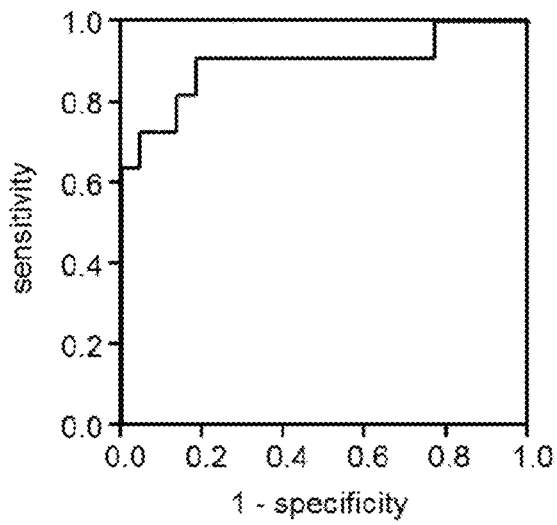
FIG. 18(A) and FIG. 18(B) each show an ROC curve of each group (NC+, MCI) versus NC− group for OxAPP672-711 (OxAβ1-40)/APP672-713 (Aβ1-42).
Figure 18:
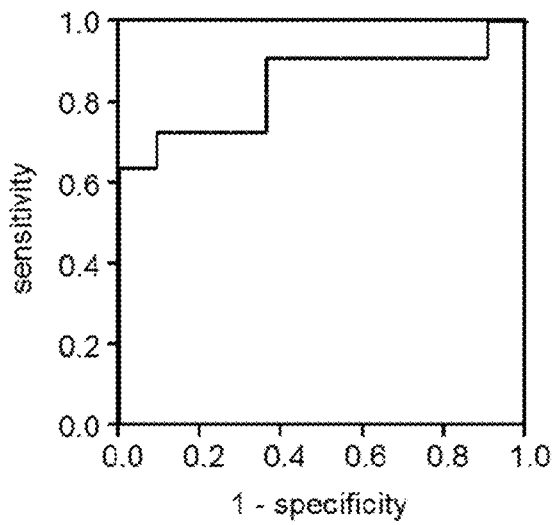
Figure 19:
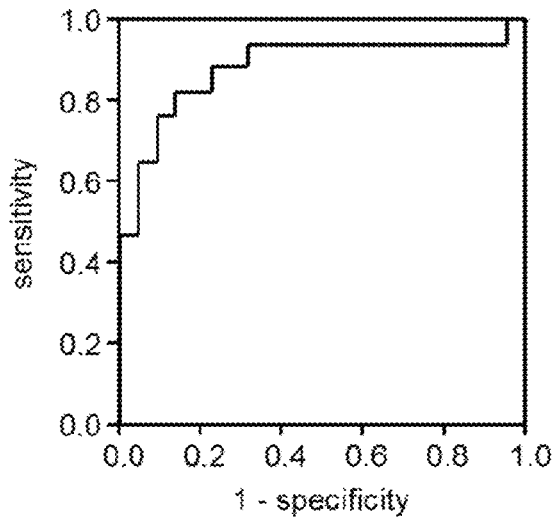
FIG. 19(C) and FIG. 19(D) each show an ROC curve of each group (AD, PiB+) versus NC− group for OxAPP672-711 (OxAβ1-40)/APP672-713 (Aβ1-42).
Figure 19:
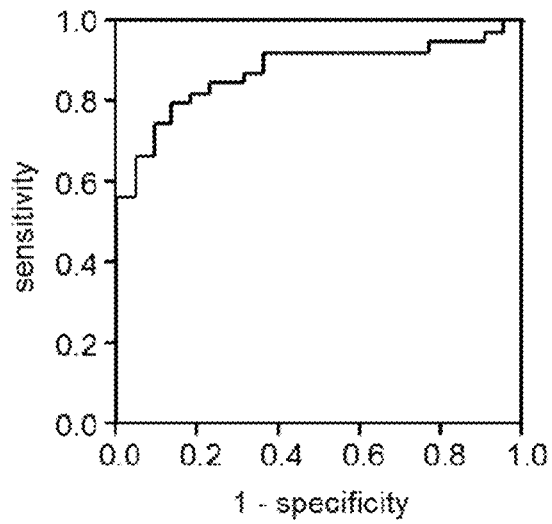

FIG. 17 is a box-and-whisker plot showing the intensity ratio of OxAPP672-711 (OxAβ1-40) to APP672-713 (Aβ1-42) in each group. FIG. 18(A), FIG. 18(B), FIG. 19(C), and FIG. 19(D) each show an ROC curve of each group (NC+, MCI, AD, PiB+) versus NC− group for OxAPP672-711 (OxAβ1-40)/APP672-713 (Aβ1-42).

Figure 20:
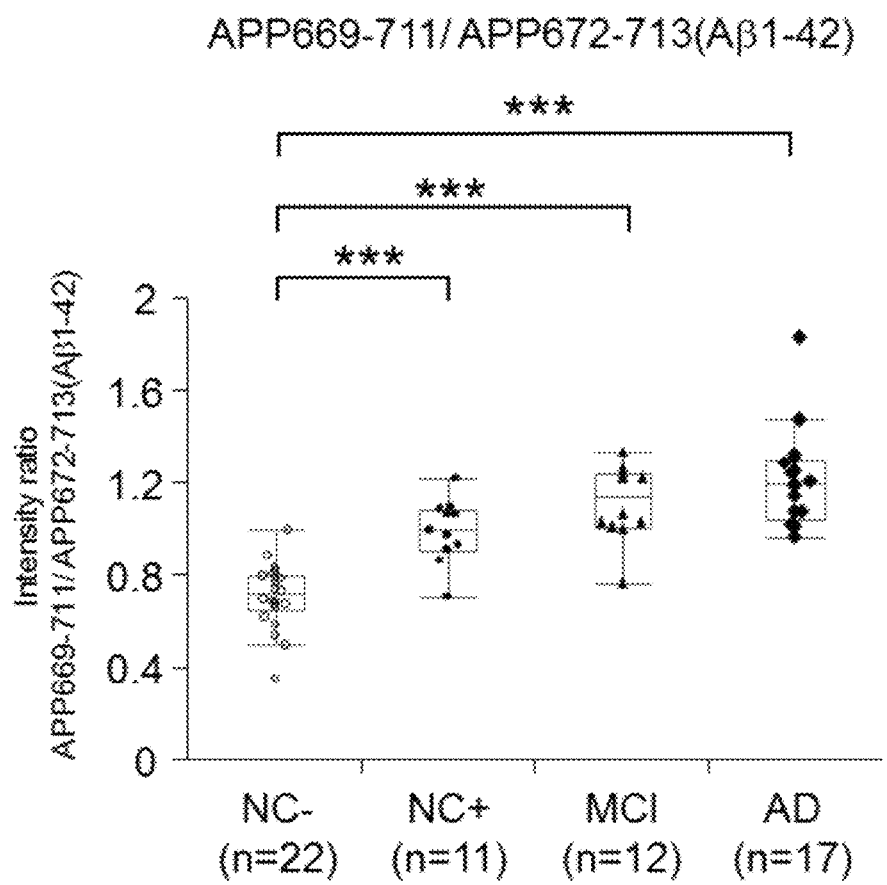
FIG. 20 is a box-and-whisker plot showing the intensity ratio of APP669-711 to APP672-713 (Aβ1-42) in each group (NC−, NC+, MCI, AD) in Example 1.
Figure 21:
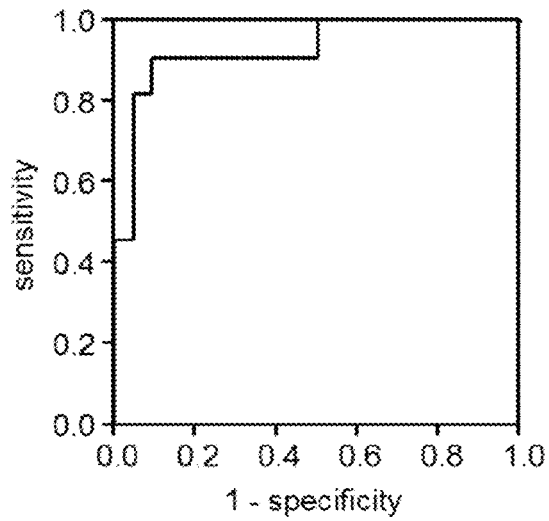
FIG. 21(A) and FIG. 21(B) each show an ROC curve of each group (NC+, MCI) versus NC− group for APP669-711/APP672-713 (Aβ1-42).
Figure 21:
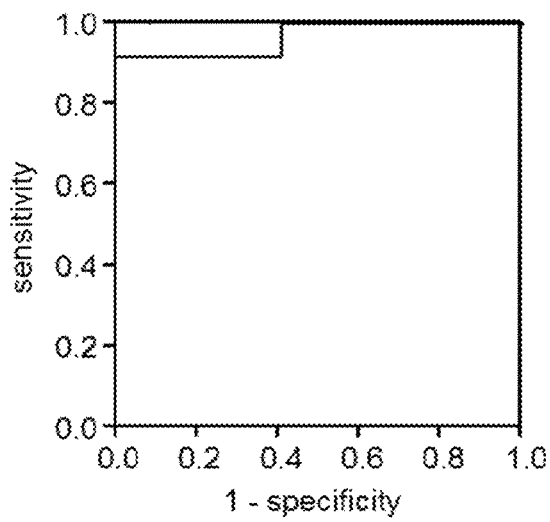
Figure 22:
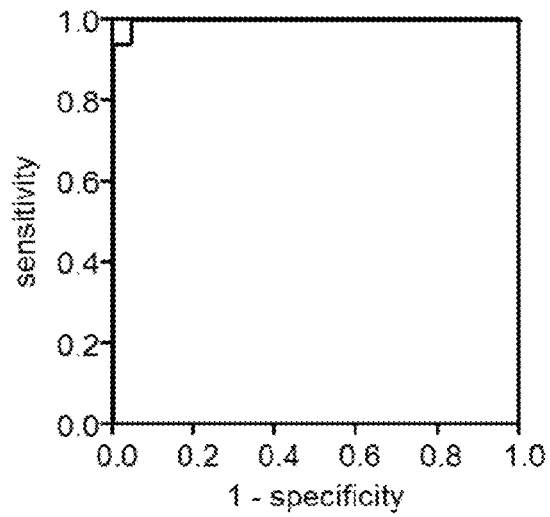
FIG. 22(C) and FIG. 22(D) each show an ROC curve of each group (AD, PiB+) versus NC− group for APP669-711/APP672-713 (Aβ1-42).
Figure 22:
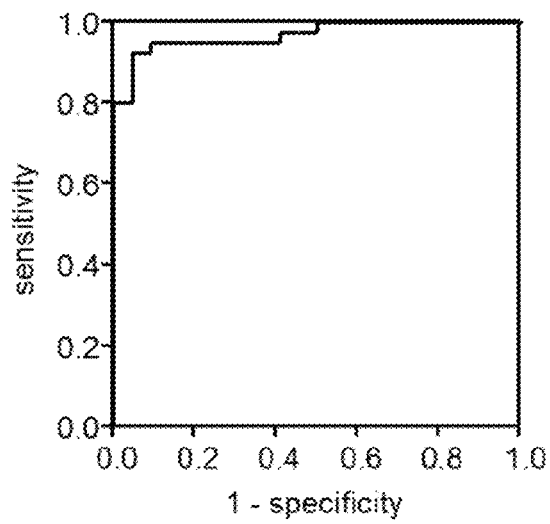

FIG. 20 is a box-and-whisker plot showing the intensity ratio of APP669-711 to APP672-713 (Aβ1-42) in each group. FIG. 21(A), FIG. 21(B), FIG. 22(C), and FIG. 22(D) each show an ROC curve of each group (NC+, MCI, AD, PiB+) versus NC− group for APP669-711/APP672-713 (Aβ1-42).

Among the nine kinds of Aβ and Aβ-like peptides detected in 60% or more cases, respective peak intensities of eight kinds other than APP672-713 (Aβ1-42) were divided by the peak intensity of APP672-713 (Aβ1-42), and the resultant values (ratios) were comparatively analyzed. As a result, in APP672-709 (Aβ1-38)/APP672-713 (Aβ1-42), APP674-711 (Aβ3-40)/APP672-713 (Aβ1-42), APP672-710 (Aβ1-39)/APP672-713 (Aβ1-42), APP672-711 (Aβ1-40)/APP672-713 (Aβ1-42), OxAPP672-711 (OxAβ1-40)/APP672-713 (Aβ1-42), and APP669-711/APP672-713 (Aβ1-42), a statistically significant increase was observed in NC+, MCI, and AD in comparison with NC− (FIGS. 5, 8, 11, 14, 17, and 20). It was demonstrated that APP669-711/APP672-713 (Aβ1-42) in particular has a strong tendency to rise as Alzheimer's disease advances (FIG. 20).

For evaluating diagnostic performances of APP672-709 (Aβ1-38)/APP672-713 (Aβ1-42), APP674-711 (Aβ3-40)/APP672-713 (Aβ1-42), APP672-710 (Aβ1-39)/APP672-713 (Aβ1-42), APP672-711 (Aβ1-40)/APP672-713 (Aβ1-42), OxAPP672-711 (OxAβ1-40)/APP672-713 (Aβ1-42), and APP669-711/APP672-713 (Aβ1-42), ROC curves of NC+, MCI, AD, and PiB+ groups versus NC− group were prepared. As a result, in all these six kinds of ratios, high AUC was observed, revealing that the ability capable of discrimination between NC− and NC+, NC− and MCI, and NC− and AD is high, and the performance capable of detecting the subject who is positive for cerebral Aβ accumulation is high [FIG. 6(A), FIG. 6(B), FIG. 7(C), and FIG. 7(D); FIG. 9(A), FIG. 9(B), FIG. 10(C), and FIG. 10(D); FIG. 12(A), FIG. 12(B), FIG. 13(C), and FIG. 13(D); FIG. 15(A), FIG. 15(B), FIG. 16(C), and FIG. 16(D); FIG. 18(A), FIG. 18(B), FIG. 19(C), and FIG. 19(D); FIG. 21(A), FIG. 21(B), FIG. 22(C), and FIG. 22(D)].

Referring to FIG. 21(A), FIG. 21(B), FIG. 22(C), and FIG. 22(D), AUC of NC+, MCI, AD versus NC− group was 0.930 or more in the ROC curve of APP669-711/APP672-713 (Aβ1-42) in particular, revealing that the ability capable of discrimination between NC− and NC+, NC− and MCI, and NC− and AD is very high. NC− vs PiB+=0.969 also revealed that the performance capable of detecting the subject who is positive for cerebral Aβ accumulation is very high. Accordingly, this suggests that these six kinds of ratios are blood markers capable of estimating a cerebral Aβ accumulation state, and thus they have a possibility capable of being used for assisting diagnosis of Alzheimer's disease.

Next, for APP672-709 (Aβ1-38)/APP672-713 (Aβ1-42), APP674-711 (Aβ3-40)/APP672-713 (Aβ1-42), APP672-710 (Aβ1-39)/APP672-713 (Aβ1-42), APP672-711 (Aβ1-40)/APP672-713 (Aβ1-42), OxAPP672-711 (OxAβ1-40)/APP672-713 (Aβ1-42), and APP669-711/APP672-713 (Aβ1-42) in which an statistically significant increase was observed in NC+, MCI, AD in comparison with NC−, discrimination of Alzheimer's disease was evaluated by setting a cut-off point. In each ROC curve in FIGS. 6, 7, 9, 10, 12, 13, 15, 16, 18, 19, 21, and 22, "each peptide/APP672-713 (Aβ1-42)" showing the highest value of "sensitivity-(1-specificity)" was set as a cut-off point. The set cut-off point, Specificity in that case, and Sensitivity, Positive Predictive Value (PPV), Negative Predictive Value (NPV), Accuracy of each group (NC+, MCI, AD, PiB+) versus NC− group are shown in Table 4.

TABLE 4

Evaluation of Diagnostic Performance

|  | Sensitivity | Positive Predictive Value, PPV | Negative Predictive Value, NPV | Accuracy |
|---|---|---|---|---|
| APP672-709(Aβ1-38)/APP672-713(Aβ1-42) Cut-off point = 7.895, Specificity = 0.682 | | | | |
| NC− vs NC+ | 1.000 | 0.611 | 1.000 | 0.788 |
| NC− vs MCI | 0.833 | 0.588 | 0.882 | 0.735 |
| NC− vs AD | 0.765 | 0.650 | 0.789 | 0.718 |
| NC− vs PiB+ | 0.850 | 0.829 | 0.714 | 0.790 |
| APP674-711(Aβ3-40)/APP672-713(Aβ1-42) Cut-off paint = 1.181, Specificity = 0.909 | | | | |
| NC− vs NC+ | 0.900 | 0.818 | 0.952 | 0.906 |
| NC− vs MCI | 0.833 | 0.833 | 0.909 | 0.882 |
| NC− vs AD | 1.000 | 0.895 | 1.000 | 0.949 |
| NC− vs PiB+ | 0.923 | 0.947 | 0.870 | 0.918 |
| APP672-710(Aβ1-39)/APP672-713(Aβ1-42) Cut-off point = 1.932, Specificity = 0.864 | | | | |
| NC− vs NC+ | 0.909 | 0.769 | 0.950 | 0.879 |
| NC− vs MCI | 0.833 | 0.769 | 0.905 | 0.853 |
| NC− vs AD | 0.941 | 0.842 | 0.950 | 0.897 |
| NC− vs PiB+ | 0.900 | 0.923 | 0.826 | 0.887 |
| APP672-711(Aβ1-40)/APP672-713(Aβ1-42) Cut-off point = 111.7, Specificity = 0.773 | | | | |
| NC− vs NC+ | 0.909 | 0.667 | 0.944 | 0.818 |
| NC− vs MCI | 0.750 | 0.643 | 0.850 | 0.765 |
| NC− vs AD | 0.647 | 0.688 | 0.739 | 0.718 |
| NC− vs PiB+ | 0.750 | 0.857 | 0.630 | 0.758 |
| OxAPP672-711(OxAβ1-40)/APP672-713(Aβ1-42) Cut-off point = 3.431, Specificity = 0.864 | | | | |
| NC− vs NC+ | 0.818 | 0.750 | 0.905 | 0.848 |
| NC− vs MCI | 0.727 | 0.727 | 0.864 | 0.818 |
| NC− vs AD | 0.824 | 0.824 | 0.864 | 0.846 |
| NC− vs PiB+ | 0.795 | 0.912 | 0.704 | 0.820 |
| APP669-711/APP672-713(Aβ1-42) Cut-off point = 0.914, Specificity = 0.955 | | | | |
| NC− vs NC+ | 0.818 | 0.900 | 0.913 | 0.909 |
| NC− vs MCI | 0.917 | 0.917 | 0.955 | 0.941 |
| NC− vs AD | 1.000 | 0.944 | 1.000 | 0.974 |
| NC− vs PiB+ | 0.925 | 0.974 | 0.875 | 0.935 |

In Table 4,
Cut-off point: cut-off point,

Positive Predictive Value (PPV)=(number of true positive)/(number of true positive+number of false positive), Negative Predictive Value (NPV)=(number of true negative)/(number of true negative+number of false negative), and Accuracy=(number of true positive+number of true negative)/number of total cases.

APP669-711/APP672-713 (Aβ1-42) shows very high numerical values in all of Specificity, Sensitivity, Positive Predictive Value (PPV), Negative Predictive Value (NPV), and Accuracy, revealing that it has high ability capable of discriminating between NC− and NC+, MCI, AD, and PiB+, and in particular, it is effective for determination of positivity of cerebral Aβ accumulation. The very high ability capable of discrimination between NC−, and NC+, MCI, and AD also indicates the applicability to assist diagnosis of Alzheimer's disease. Regarding other five kinds of ratios, they show high values in Specificity, Sensitivity, Positive Predictive Value (PPV), Negative Predictive Value (NPV), or Accuracy, revealing that they have high ability capable of discrimination between NC− and NC+, MCI, AD, and PiB+, and in particular, they show the possibility effective for determination of positivity of cerebral Aβ accumulation. The high ability capable of discrimination between NC− and NC+, MCI, and AD also indicates the applicability to assist diagnosis of Alzheimer's disease.

(6) Correlation Analysis with PiB Measurement Value

Cerebral Aβ accumulation is an important pathological index for Alzheimer's disease, and excessive accumulation of Aβ is known to begin far in advance of exteriorization of dementia. PiB is a radioactive agent that specifically binds with Aβ aggregate, and by measuring accumulation of PiB with the use of PET, it is possible to form an image of the cerebral Aβ accumulation. In order to investigate whether APP669-711/APP672-713 (Aβ1-42) in plasma, which shows the ability capable of determining with high accuracy a subject who is positive for cerebral Aβ accumulation, reflects a cerebral Aβ accumulation state, correlation between APP669-711/APP672-713 (Aβ1-42) and PiB accumulation mean value of cortical region (mcSUVR: mean cortical Standard Uptake Value Ratio) was analyzed.

Figure 23:
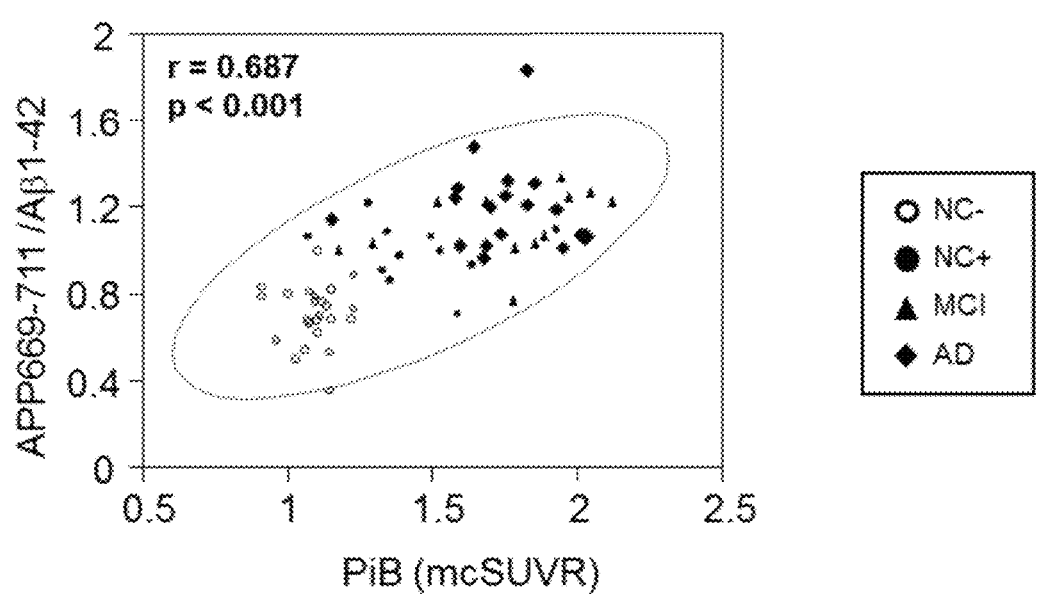
FIG. 23 is a scatter diagram of PiB accumulation mean value of cortical region (mcSUVR: mean cortical Standard Uptake Value Ratio) and APP669-711/APP672-713 (Aβ1-42) in a total of 62 cases in Example 1. A probability ellipse (p=0.95) is indicated by a curve.

FIG. 23 is a scatter diagram for a total of 62 cases, in which the horizontal axis represents the PiB accumulation mean value (mcSUVR) and the vertical axis represents APP669-711/APP672-713 (Aβ1-42) ratio.

The PiB accumulation mean value was measured by quantifying PiB accumulation of the cortex, and determining accumulation ratio of the cerebrum on the basis of the cerebellum. Correlation between APP669-711/APP672-713 (Aβ1-42) ratio obtained by IP-MS and PiB accumulation mean value (mcSUVR) obtained by PET was evaluated with Pearson product-moment correlation coefficient. As a result, the correlation coefficient (r) was 0.687, $p<0.001$ (FIG. 23).

It was revealed that there is a significantly strong correlation between APP669-711/APP672-713 (Aβ1-42) ratio and PiB accumulation mean value (mcSUVR). This means that APP669-711/APP672-713 (Aβ1-42) ratio in plasma reflects a cerebral Aβ accumulation state, and indicates that it has the possibility capable of being used as a blood marker for determining a cerebral Aβ accumulation state.

The results demonstrated above indicate that the marker of the present invention is useful as a blood marker for determining a cerebral Aβ accumulation state. This also has indicated the applicability to assist diagnosis of Alzheimer's disease and to presymptomatically diagnose Alzheimer's disease.

The invention claimed is:

1. A method for detecting an amyloid precursor protein (APP)-derived peptide, the method comprising:
    detecting, in a sample, the APP-derived peptide that is APP669-711 (SEQ ID NO.: 7),
    wherein the sample is selected from the group consisting of blood, plasma, urine, saliva, sputum, and feces.

2. The method according to claim 1, further comprising detecting APP672-713 (Aβ1-42) (SEQ ID NO.: 6).

3. The method according to claim 1, wherein the detecting comprises capturing said APP-derived peptide by an antibody-immobilizing bead.

4. The method according to claim 1, wherein the detecting comprises capturing said APP-derived peptide by an antibody-immobilizing bead prior to detection by mass spectrometer.

5. The method according to claim 1, wherein the detecting comprises capturing said APP-derived peptide by an antibody-immobilizing bead and detecting said APP-derived peptide by mass spectrometer.

6. The method according to claim 1, further comprising detecting OxAPP672-711 (OxAβ1-40) (SEQ ID NO.: 5).

7. The method according to claim 1, wherein the sample is from human.

8. The method according to claim 1, wherein the sample is blood.

9. The method according to claim 1, further comprising detecting APP674-711 (Aβ3-40) (SEQ ID NO.: 2).

10. The method according to claim 1, wherein the sample is plasma.

* * * * *

```
                           SEQUENCE LISTING

<160> NUMBER OF SEQ ID NOS: 7

<210> SEQ ID NO 1
<211> LENGTH: 38
<212> TYPE: PRT
<213> ORGANISM: Homo Sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly
        35

<210> SEQ ID NO 2
<211> LENGTH: 38
<212> TYPE: PRT
<213> ORGANISM: Homo Sapiens

<400> SEQUENCE: 2

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 3
<211> LENGTH: 39
<212> TYPE: PRT
<213> ORGANISM: Homo Sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val
        35

<210> SEQ ID NO 4
<211> LENGTH: 40
<212> TYPE: PRT
<213> ORGANISM: Homo Sapiens

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 5
<211> LENGTH: 40
<212> TYPE: PRT
```

```
<213> ORGANISM: Homo Sapiens

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 6
<211> LENGTH: 42
<212> TYPE: PRT
<213> ORGANISM: Homo Sapiens

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 7
<211> LENGTH: 43
<212> TYPE: PRT
<213> ORGANISM: Homo Sapiens

<400> SEQUENCE: 7

Val Lys Met Asp Ala Glu Phe Arg His Asp Ser Gly Tyr Glu Val His
1               5                   10                  15

His Gln Lys Leu Val Phe Phe Ala Glu Asp Val Gly Ser Asn Lys Gly
            20                  25                  30

Ala Ile Ile Gly Leu Met Val Gly Gly Val Val
        35                  40
```